US012778449B2

(12) United States Patent
Addison et al.

(10) Patent No.: US 12,778,449 B2
(45) **Date of Patent: *Nov. 3, 2026**

(54) DEPTH SENSING VISUALIZATION MODES FOR NON-CONTACT MONITORING

(71) Applicant: Covidien LP, Mansfield, MA (US)

(72) Inventors: Paul S. Addison, Edinburgh (GB); Dominique Jacquel, Edinburgh (GB); Philip Smit, Hamilton (GB)

(73) Assignee: Covidien LP, Mansfield, MA (US)

( * ) Notice: Subject to any disclaimer, the term of this patent is extended or adjusted under 35 U.S.C. 154(b) by 209 days.

This patent is subject to a terminal disclaimer.

(21) Appl. No.: 18/892,052

(22) Filed: Sep. 20, 2024

(65) Prior Publication Data

US 2025/0009254 A1 Jan. 9, 2025

Related U.S. Application Data

(63) Continuation of application No. 18/173,008, filed on Feb. 22, 2023, now Pat. No. 12,121,342, which is a continuation of application No. 16/713,265, filed on Dec. 13, 2019, now Pat. No. 11,617,520.

(60) Provisional application No. 62/779,964, filed on Dec. 14, 2018.

(51) Int. Cl.

| | |
|---|---|
| ***G06K 9/00*** | (2022.01) |
| ***A61B 5/00*** | (2006.01) |
| ***A61B 5/091*** | (2006.01) |
| ***G06T 7/00*** | (2017.01) |
| ***G06T 7/55*** | (2017.01) |

(52) U.S. Cl.

CPC .............. *A61B 5/091* (2013.01); *A61B 5/742* (2013.01); *A61B 5/746* (2013.01); *G06T 7/0012* (2013.01); *G06T 7/55* (2017.01); *G06T 2207/10016* (2013.01); *G06T 2207/30061* (2013.01)

(58) Field of Classification Search

USPC ....... 382/100, 103, 128–131, 156, 168, 181, 382/254, 305, 312; 600/407, 534, 538

See application file for complete search history.

(56) References Cited

U.S. PATENT DOCUMENTS

| | | | | |
|---|---|---|---|---|
| 7,431,700 | B2 | 10/2008 | Aoki et al. | |
| 9,204,823 | B2 | 12/2015 | Derenne et al. | |
| 9,226,691 | B2 | 1/2016 | Bernal et al. | |
| 9,339,210 | B2 | 5/2016 | Kersten et al. | |
| 9,983,770 | B2 * | 5/2018 | Zheng | G06F 3/0484 |
| 10,201,293 | B2 | 2/2019 | Bernal et al. | |

(Continued)

*Primary Examiner* — Seyed H Azarian

(74) *Attorney, Agent, or Firm* — Dymera IP, LLC

(57) ABSTRACT

The present invention relates to the field of medical monitoring, and, in particular, to non-contact detecting and monitoring of patient breathing. Systems, methods, and computer readable media are described for calculating a change in depth of a region of interest (ROI) on a patient and assigning one or more visual indicators to at least a portion of a graphic based on the calculated changes in depth and/or based on a tidal volume signal generated for the patient. In some embodiments, the systems, methods, and/or computer readable media can display the visual indicators overlaid onto at least the portion in real-time and/or can display the tidal volume signal in real-time. The systems, methods, and/or computer readable media can trigger an alert and/or an alarm when a breathing abnormality is detected.

16 Claims, 22 Drawing Sheets
(15 of 22 Drawing Sheet(s) Filed in Color)

(56) References Cited

U.S. PATENT DOCUMENTS

| | | | | |
|---|---|---|---|---|
| 10,219,739 | B2 | 3/2019 | Mestha | |
| 10,702,188 | B2 * | 7/2020 | Addison | A61B 5/1032 |
| 10,939,824 | B2 | 3/2021 | Addison | |
| 11,311,252 | B2 | 4/2022 | Jacquel et al. | |
| 11,315,275 | B2 | 4/2022 | Addison et al. | |
| 11,328,572 | B2 | 5/2022 | Addison et al. | |
| 11,350,850 | B2 | 6/2022 | Jacquel et al. | |
| 11,484,208 | B2 | 11/2022 | Addison | |
| 11,504,072 | B2 | 11/2022 | Addison et al. | |
| 11,510,584 | B2 | 11/2022 | Addison et al. | |
| 11,617,520 | B2 | 4/2023 | Addison et al. | |
| 11,623,044 | B2 | 4/2023 | Addison | |
| 11,712,176 | B2 | 8/2023 | Addison et al. | |
| 2010/0249630 | A1 | 9/2010 | Droitcour et al. | |
| 2011/0144517 | A1 | 6/2011 | Cervantes | |
| 2014/0140592 | A1 * | 5/2014 | Lasenby | G01B 11/16<br>382/128 |
| 2015/0094597 | A1 * | 4/2015 | Mestha | A61B 5/7282<br>600/407 |
| 2015/0265187 | A1 * | 9/2015 | Bernal | A61B 5/1128<br>600/534 |
| 2018/0053392 | A1 * | 2/2018 | White | A61B 5/0077 |
| 2019/0133499 | A1 * | 5/2019 | Auerbach | A61B 5/0077 |
| 2022/0007966 | A1 | 1/2022 | Jacquel et al. | |
| 2022/0167880 | A1 | 6/2022 | Addison et al. | |
| 2022/0225893 | A1 | 7/2022 | Miller et al. | |
| 2022/0233096 | A1 | 7/2022 | Smit et al. | |
| 2022/0240790 | A1 | 8/2022 | Smit et al. | |
| 2023/0000584 | A1 | 1/2023 | Jacquel et al. | |
| 2023/0082016 | A1 | 3/2023 | Montgomery et al. | |
| 2023/0095345 | A1 | 3/2023 | Smit et al. | |
| 2023/0112712 | A1 | 4/2023 | Montgomery et al. | |
| 2023/0187058 | A1 | 6/2023 | Smit et al. | |
| 2023/0190131 | A1 | 6/2023 | Smit et al. | |
| 2023/0196797 | A1 | 6/2023 | Addison et al. | |
| 2023/0310865 | A1 | 10/2023 | Addison et al. | |
| 2023/0329590 | A1 | 10/2023 | Nelson et al. | |
| 2023/0397843 | A1 | 12/2023 | Addison et al. | |
| 2024/0016440 | A1 | 1/2024 | Miller et al. | |
| 2024/0115216 | A1 | 4/2024 | Addison et al. | |
| 2024/0119819 | A1 | 4/2024 | Addison et al. | |
| 2024/0127469 | A1 | 4/2024 | Montgomery et al. | |
| 2024/0188882 | A1 | 6/2024 | Addison et al. | |
| 2024/0212200 | A1 | 6/2024 | Jiang et al. | |
| 2024/0350226 | A1 | 10/2024 | Sethi et al. | |

* cited by examiner

DEPTH SENSING VISUALIZATION MODES FOR NON-CONTACT MONITORING

CROSS-REFERENCE TO RELATED APPLICATIONS

The present application is a continuation of U.S. patent application Ser. No. 18/173,008, filed Feb. 22, 2023; which is a continuation of U.S. patent application Ser. No. 16/713,265, filed Dec. 13, 2019, now U.S. Pat. No. 11,617,520, which claims the benefit of priority to U.S. Provisional Patent Application No. 62/779,964, filed Dec. 14, 2018, the entire disclosures of which are incorporated herein by reference in their entireties.

FIELD

The present technology is generally related to non-contact patient monitoring.

BACKGROUND

Many conventional medical monitors require attachment of a sensor to a patient in order to detect physiologic signals from the patient and to transmit detected signals through a cable to the monitor. These monitors process the received signals and determine vital signs such as the patient's pulse rate, respiration rate, and arterial oxygen saturation. For example, a pulse oximeter is a finger sensor that can include two light emitters and a photodetector. The sensor emits light into the patient's finger and transmits the detected light signal to a monitor. The monitor includes a processor that processes the signal, determines vital signs (e.g., pulse rate, respiration rate, arterial oxygen saturation), and displays the vital signs on a display.

Other monitoring systems include other types of monitors and sensors, such as electroencephalogram (EEG) sensors, blood pressure cuffs, temperature probes, air flow measurement devices (e.g., spirometer), and others. Some wireless, wearable sensors have been developed, such as wireless EEG patches and wireless pulse oximetry sensors.

Video-based monitoring is a field of patient monitoring that uses one or more remote video cameras to detect physical attributes of the patient. This type of monitoring can also be called "non-contact" monitoring in reference to the remote video sensor(s), which does/do not contact the patient. The remainder of this disclosure offers solutions and improvements in this field.

SUMMARY

The techniques of this disclosure generally relate to non-contact, video-based patient monitoring, wherein at least one region of interest (ROI) of a patient is defined, and wherein at least one image capture device captures two or more images of the ROI. A processor calculates a change in depth of at least one portion of the ROI within the two or more images and assigns a visual indicator to a display based at least in part on the calculated change in depth.

In another aspect, the disclosure provides for assignment of the visual indicator based on a sign of the change in depth or magnitude of the change in depth, including average or instantaneous average change in depth over time. In other aspects, the visual indicator includes a color, shade, pattern, concentration and/or an intensity. In other aspects, the visual indicator is overlaid onto a portion of the ROI. In other aspects, the visual indicator is overlaid in real time. In other aspects, the tidal volume signal is displayed in real time.

In another aspects, a graphic is provided with a visual indicator when the tidal volume indicates that a patient is inhaling and/or exhaling. In other aspects, the monitoring system provides for threshold target tidal volumes, representing risks of hypoventilation, hyperventilation, obstructive lung disease indication, etc.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted but are for explanation and understanding only.

DETAILED DESCRIPTION

Figure 1:
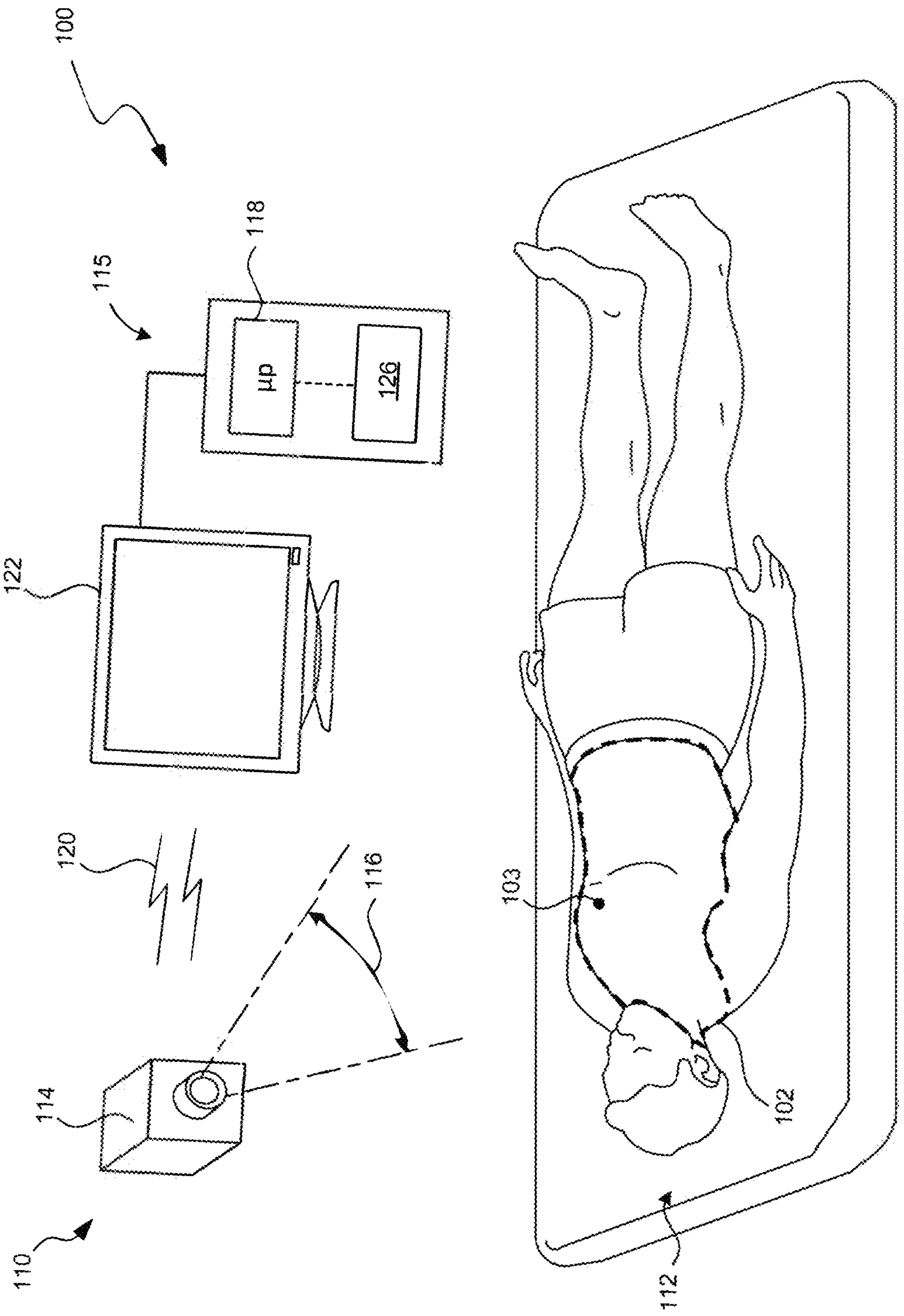
FIG. 1 is a schematic view of a video-based patient monitoring system configured in accordance with various embodiments of the present technology.

The following disclosure describes video-based patient monitoring systems and associated methods for detecting and/or monitoring patient breathing and related parameters. As described in greater detail below, systems and/or methods configured in accordance with embodiments of the present technology are configured to recognize and/or identify a patient and to define one or more regions of interest (ROI's) on the patient. Additionally or alternatively, the system and/or methods are configured to capture one or more images (e.g., a video sequence) of the ROI's and/or to measure changes in depth of regions (e.g., one or more pixels or groups of pixels) in the ROI's over time. Based, at least in part, on these measurements, the systems and/or methods can assign one or more visual indicators to regions of one or more of the ROI's. In these and other embodiments, the systems and/or methods generate various breathing parameter signals of all or a subset of the ROI's. The breathing parameter signals can include tidal volume, minute volume, and/or respiratory rate, among others. In these and other embodiments, the systems and/or methods can analyze the generated signals and can trigger alerts and/or alarms when the systems and/or methods detect one or more breathing abnormalities. In these and still other embodiments, the systems and/or methods can display (e.g., in real-time) all or a subset of the assigned visual indicator(s) and/or of the generated signals on a display, e.g., to provide a user (e.g., a caregiver, a clinician, a patient, etc.) a visual indication of the patient's breathing. For example, the systems and/or methods can overlay the assigned visual indicator(s) onto the captured images of the patient to indicate: (i) whether the patient is breathing; and/or, (ii) whether a patient's breathing is abnormal.

Specific details of several embodiments of the present technology are described herein with reference to FIGS. 1-25. Although many of the embodiments are described with respect to devices, systems, and methods for video-based detection and/or monitoring of breathing in a human patient, other applications and other embodiments in addition to those described herein are within the scope of the present technology. For example, at least some embodiments of the present technology can be useful for video-based detection and/or monitoring of breathing in other animals and/or in non-patients (e.g., elderly or neonatal individuals within their homes). It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

FIG. 1 is a schematic view of a patient 112 and a video-based patient monitoring system 100 configured in accordance with various embodiments of the present technology. The system 100 includes a non-contact detector 110 and a computing device 115. In some embodiments, the detector 110 can include one or more image capture devices, such as one or more video cameras. In the illustrated embodiment, the non-contact detector 110 includes a video camera 114. The non-contact detector 110 of the system 100 is placed remote from the patient 112. More specifically, the video camera 114 of the non-contact detector 110 is positioned remote from the patient 112 in that it is spaced apart from and does not contact the patient 112. The camera 114 includes a detector exposed to a field of view (FOV) 116 that encompasses at least a portion of the patient 112.

The camera 114 can capture a sequence of images over time. The camera 114 can be a depth sensing camera, such as a Kinect camera from Microsoft Corp. (Redmond, Washington). A depth sensing camera can detect a distance between the camera and objects within its field of view. Such information can be used, as disclosed herein, to determine that a patient 112 is within the FOV 116 of the camera 114 and/or to determine one or more ROI's to monitor on the patient 112. Once a ROI is identified, the ROI can be monitored over time, and the changes in depth of regions (e.g., pixels) within the ROI 102 can represent movements of the patient 112 associated with breathing. As described in greater detail in U.S. Provisional Patent Application Ser. No. 62/614,763, those movements, or changes of regions within the ROI 102, can be used to determine various breathing parameters, such as tidal volume, minute volume, respiratory rate, etc. Those movements, or changes of regions within the ROI 102, can also be used to detect various breathing abnormalities, as discussed in greater detail in U.S. Provisional Patent Application Ser. No. 62/716,724. The various breathing abnormalities can include, for example, apnea, rapid breathing (tachypnea), slow breathing, intermittent or irregular breathing, shallow breathing, obstructed and/or impaired breathing, and others. U.S. Provisional Patent Application Ser. Nos. 62/614,763 and 62/716,724 are incorporated herein by reference in their entirety.

In some embodiments, the system 100 determines a skeleton-like outline of the patient 112 to identify a point or points from which to extrapolate a ROI. For example, a skeleton-like outline can be used to find a center point of a chest, shoulder points, waist points, and/or any other points on a body of the patient 112. These points can be used to determine one or more ROI's. For example, a ROI 102 can be defined by filling in area around a center point 103 of the chest, as shown in FIG. 1. Certain determined points can define an outer edge of the ROI 102, such as shoulder points. In other embodiments, instead of using a skeleton, other points are used to establish a ROI. For example, a face can be recognized, and a chest area inferred in proportion and spatial relation to the face. In other embodiments, a reference point of a patient's chest can be obtained (e.g., through a previous 3-D scan of the patient), and the reference point can be registered with a current 3-D scan of the patient. In these and other embodiments, the system 100 can define a ROI around a point using parts of the patient 112 that are within a range of depths from the camera 114. In other words, once the system 100 determines a point from which to extrapolate a ROI, the system 100 can utilize depth information from the depth sensing camera 114 to fill out the ROI. For example, if the point 103 on the chest is selected, parts of the patient 112 around the point 103 that are a similar depth from the camera 114 as the point 103 are used to determine the ROI 102.

In another example, the patient 112 can wear specially configured clothing (not shown) that includes one or more features to indicate points on the body of the patient 112, such as the patient's shoulders and/or the center of the patient's chest. The one or more features can include visually encoded message (e.g., bar code, QR code, etc.), and/or brightly colored shapes that contrast with the rest of the patient's clothing. In these and other embodiments, the one or more features can include one or more sensors that are configured to indicate their positions by transmitting light or other information to the camera 114. In these and still other embodiments, the one or more features can include a grid or another identifiable pattern to aid the system 100 in recognizing the patient 112 and/or the patient's movement. In some embodiments, the one or more features can be stuck on the clothing using a fastening mechanism such as adhesive, a pin, etc. For example, a small sticker can be placed on a patient's shoulders and/or on the center of the patient's chest that can be easily identified within an image captured by the camera 114. The system 100 can recognize the one or more features on the patient's clothing to identify specific points on the body of the patient 112. In turn, the system 100 can use these points to recognize the patient 112 and/or to define a ROI.

In some embodiments, the system 100 can receive user input to identify a starting point for defining a ROI. For example, an image can be reproduced on a display 122 of the system 100, allowing a user of the system 100 to select a patient 112 for monitoring (which can be helpful where multiple objects are within the FOV 116 of the camera 114) and/or allowing the user to select a point on the patient 112 from which a ROI can be determined (such as the point 103 on the chest of the patient 112). In other embodiments, other methods for identifying a patient 112, identifying points on the patient 112, and/or defining one or more ROI's can be used.

Figure 2:
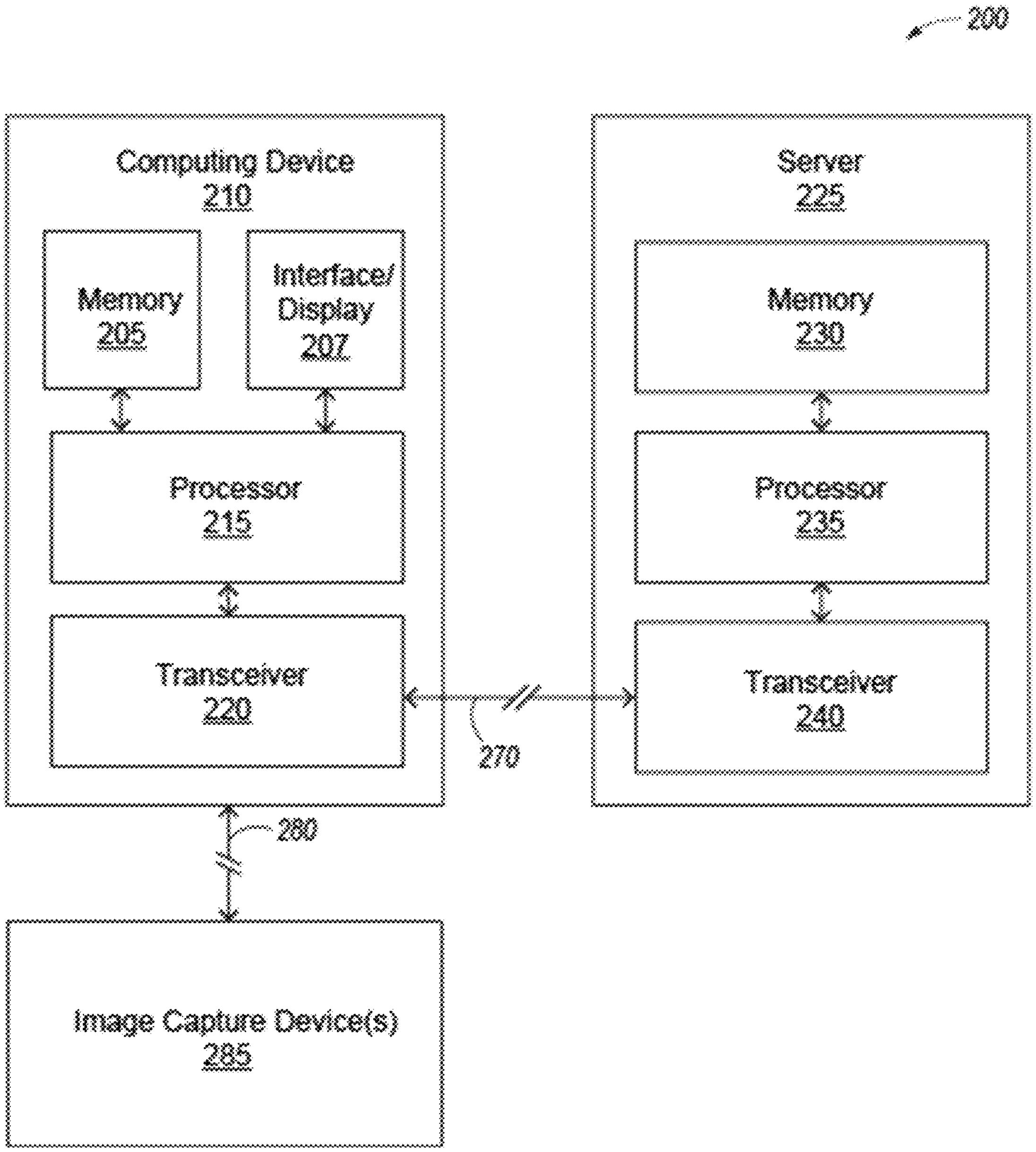
FIG. 2 is a block diagram illustrating a video-based patient monitoring system having a computing device, a server, and one or more image capture devices, and configured in accordance with various embodiments of the present technology.

The images detected by the camera 114 can be sent to the computing device 115 through a wired or wireless connection 120. The computing device 115 can include a processor 118 (e.g., a microprocessor), the display 122, and/or hardware memory 126 for storing software and computer instructions. Sequential image frames of the patient 112 are recorded by the video camera 114 and sent to the processor 118 for analysis. The display 122 can be remote from the camera 114, such as a video screen positioned separately from the processor 118 and the memory 126. Other embodiments of the computing device 115 can have different, fewer, or additional components than shown in FIG. 1. In some embodiments, the computing device 115 can be a server. In other embodiments, the computing device 115 of FIG. 1 can be additionally connected to a server (e.g., as shown in FIG. 2 and discussed in greater detail below). The captured images/video can be processed or analyzed at the computing device 115 and/or a server to determine a variety of parameters (e.g., tidal volume, minute volume, respiratory rate, etc.) of a patient's breathing.

FIG. 2 is a block diagram illustrating a video-based patient monitoring system 200 (e.g., the video-based patient monitoring system 100 shown in FIG. 1) having a computing device 210, a server 225, and one or more image capture devices 285, and configured in accordance with various embodiments of the present technology. In various embodiments, fewer, additional, and/or different components can be used in the system 200. The computing device 210 includes a processor 215 that is coupled to a memory 205. The processor 215 can store and recall data and applications in the memory 205, including applications that process information and send commands/signals according to any of the methods disclosed herein. The processor 215 can also (i) display objects, applications, data, etc. on an interface/display 207 and/or (ii) receive inputs through the interface/display 207. As shown, the processor 215 is also coupled to a transceiver 220.

The computing device 210 can communicate with other devices, such as the server 225 and/or the image capture device(s) 285 via (e.g., wired or wireless) connections 270 and/or 280, respectively. For example, the computing device 210 can send to the server 225 information determined about a patient from images captured by the image capture device(s) 285. The computing device 210 can be the computing device 115 of FIG. 1. Accordingly, the computing device 210 can be located remotely from the image capture device(s) 285, or it can be local and close to the image capture device(s) 285 (e.g., in the same room). In various embodiments disclosed herein, the processor 215 of the computing device 210 can perform the steps disclosed herein. In other embodiments, the steps can be performed on a processor 235 of the server 225. In some embodiments, the various steps and methods disclosed herein can be performed by both of the processors 215 and 235. In some embodiments, certain steps can be performed by the processor 215 while others are performed by the processor 235. In some embodiments, information determined by the processor 215 can be sent to the server 225 for storage and/or further processing.

In some embodiments, the image capture device(s) 285 are remote sensing device(s), such as depth sensing video camera(s), as described above with respect to FIG. 1. In some embodiments, the image capture device(s) 285 can be or include some other type(s) of device(s), such as proximity sensors or proximity sensor arrays, heat or infrared sensors/cameras, sound/acoustic or radio wave emitters/detectors, or other devices that include a field of view and can be used to monitor the location and/or characteristics of a patient or a region of interest (ROI) on the patient. Body imaging technology can also be utilized according to the methods disclosed herein. For example, backscatter x-ray or millimeter wave scanning technology can be utilized to scan a patient, which can be used to define and/or monitor a ROI. Advantageously, such technologies can be able to "see" through clothing, bedding, or other materials while giving an accurate representation of the patient's skin. This can allow for more accurate measurements, particularly if the patient is wearing baggy clothing or is under bedding. The image capture device(s) 285 can be described as local because they are relatively close in proximity to a patient such that at least a part of a patient is within the field of view of the image capture device(s) 285. In some embodiments, the image capture device(s) 285 can be adjustable to ensure that the patient is captured in the field of view. For example, the image capture device(s) 285 can be physically movable, can have a changeable orientation (such as by rotating or panning), and/or can be capable of changing a focus, zoom, or other characteristic to allow the image capture device(s) 285 to adequately capture images of a patient and/or a ROI of the patient. In various embodiments, for example, the image capture device(s) 285 can focus on a ROI, zoom in on the ROI, center the ROI within a field of view by moving the image capture device(s) 285, or otherwise adjust the field of view to allow for better and/or more accurate tracking/measurement of the ROI.

The server 225 includes a processor 235 that is coupled to a memory 230. The processor 235 can store and recall data and applications in the memory 230. The processor 235 is also coupled to a transceiver 240. In some embodiments, the processor 235, and subsequently the server 225, can communicate with other devices, such as the computing device 210 through the connection 270.

The devices shown in the illustrative embodiment can be utilized in various ways. For example, either the connections 270 and 280 can be varied. Either of the connections 270 and 280 can be a hard-wired connection. A hard-wired connection can involve connecting the devices through a USB (universal serial bus) port, serial port, parallel port, or other type of wired connection that can facilitate the transfer of data and information between a processor of a device and a second processor of a second device. In another embodiment, either of the connections 270 and 280 can be a dock where one device can plug into another device. In other embodiments, either of the connections 270 and 280 can be a wireless connection. These connections can take the form of any sort of wireless connection, including, but not limited to, Bluetooth connectivity, Wi-Fi connectivity, infrared, visible light, radio frequency (RF) signals, or other wireless protocols/methods. For example, other possible modes of wireless communication can include near-field communications, such as passive radio-frequency identification (RFID) and active RFID technologies. RFID and similar near-field communications can allow the various devices to communicate in short range when they are placed proximate to one another. In yet another embodiment, the various devices can connect through an internet (or other network) connection. That is, either of the connections 270 and 280 can represent several different computing devices and network components that allow the various devices to communicate through the internet, either through a hard-wired or wireless connection. Either of the connections 270 and 280 can also be a combination of several modes of connection.

The configuration of the devices in FIG. 2 is merely one physical system 200 on which the disclosed embodiments can be executed. Other configurations of the devices shown can exist to practice the disclosed embodiments. Further, configurations of additional or fewer devices than the devices shown in FIG. 2 can exist to practice the disclosed embodiments. Additionally, the devices shown in FIG. 2 can be combined to allow for fewer devices than shown or can be separated such that more than the three devices exist in a system. It will be appreciated that many various combinations of computing devices can execute the methods and systems disclosed herein. Examples of such computing devices can include other types of medical devices and sensors, infrared cameras/detectors, night vision cameras/detectors, other types of cameras, augmented reality goggles, virtual reality goggles, mixed reality goggle, radio frequency transmitters/receivers, smart phones, personal computers, servers, laptop computers, tablets, blackberries, RFID enabled devices, smart watch or wearables, or any combinations of such devices.

Figure 3:
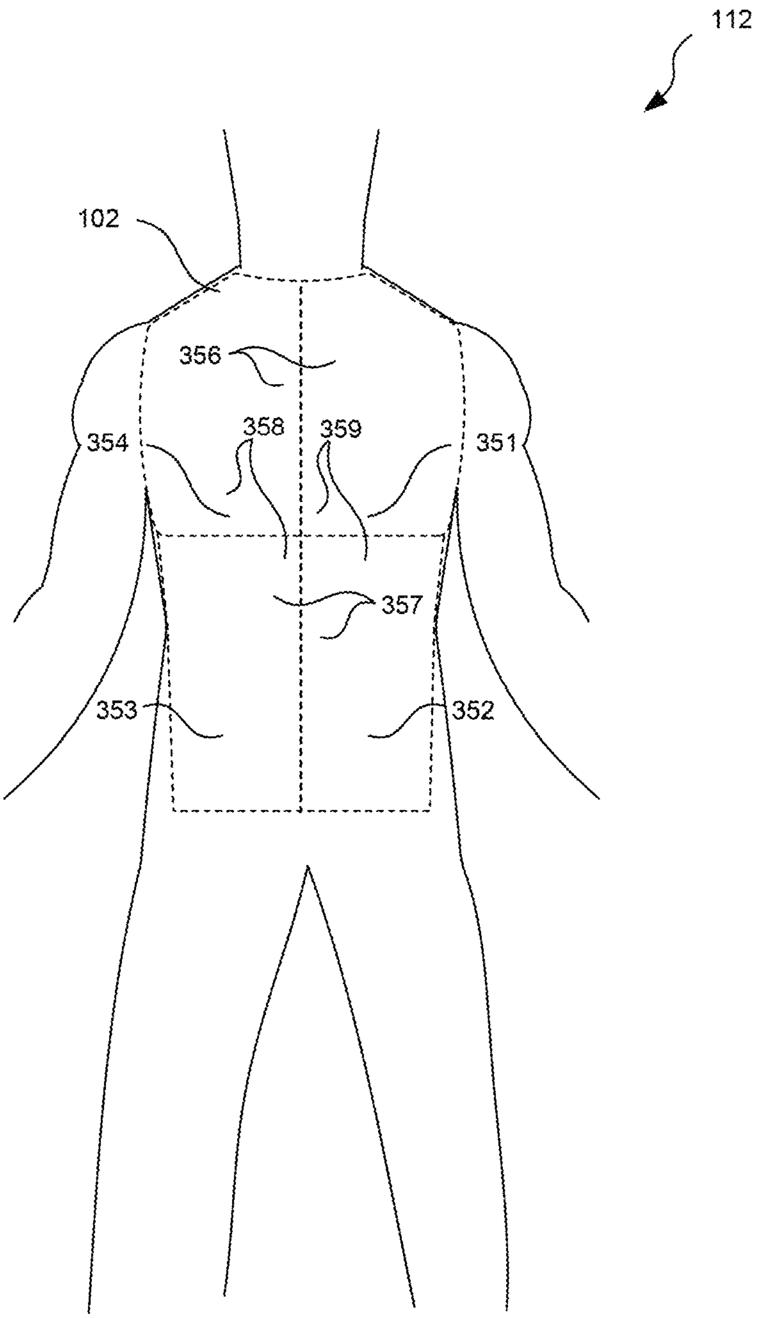
FIG. 3 is a schematic view of a patient showing various regions of interest that can be defined by video-based patient monitoring systems configured in accordance with various embodiments of the present technology.

FIG. 3 is a schematic view of a patient 112 showing various regions of interest (ROI's) that can be defined by video-based patient monitoring systems configured in accordance with various embodiments of the present technology. As discussed above, a video-based patient monitoring system can define a ROI using a variety of methods (e.g., using extrapolation from a point on the patient 112, using inferred positioning from proportional and/or spatial relationships with the patient's face, using parts of the patient 112 having similar depths from the camera 114 as a point, using one or more features on the patient's clothing, using user input, etc.). In some embodiments, the video-based patient monitoring system can define an aggregate ROI 102 that includes both sides of the patient's chest as well as both sides of the patient's abdomen. As discussed in greater detail below, the aggregate ROI 102 can be useful in determining a patient's aggregate tidal volume, minute volume, and/or respiratory rate, among other aggregate breathing parameters. In these and other embodiments, the system 100 can define one or more smaller regions of interest within the patient's torso. For example, the system 100 can define ROI's 351-354. As shown, ROI 351 corresponds to the left half of the patient's chest, ROI 352 corresponds to the left half of the patient's abdomen, ROI 353 corresponds to the right half of the patient's abdomen, and ROI 354 corresponds to the right half of the patient's chest.

In these and other embodiments, the system 100 can define other regions of interest in addition to or in lieu of the ROI's 102, 351, 352, 353, and/or 354. For example, the system 100 can define a ROI 356 corresponding to the patient's chest (e.g., the ROI 351 plus the ROI 354) and/or a ROI 357 corresponding to the patient's abdomen (e.g., the ROI 352 plus the ROI 353). In these and other embodiments, the system 100 can define a ROI 358 corresponding to the right side of the patient's chest or torso (e.g., the ROI 353 and/or the ROI 354) and/or a ROI 359 corresponding to the left side of the patient's chest or torso (e.g., the ROI 351 and/or the ROI 352). In these and still other embodiments, the system 100 can define one or more other regions of interest than shown in FIG. 3. For example, the system 100 can define a region of interest that includes other parts of the patient's body, such as at least a portion of the patient's neck (e.g., to detect when the patient 112 is straining to breathe).

Figure 4A:
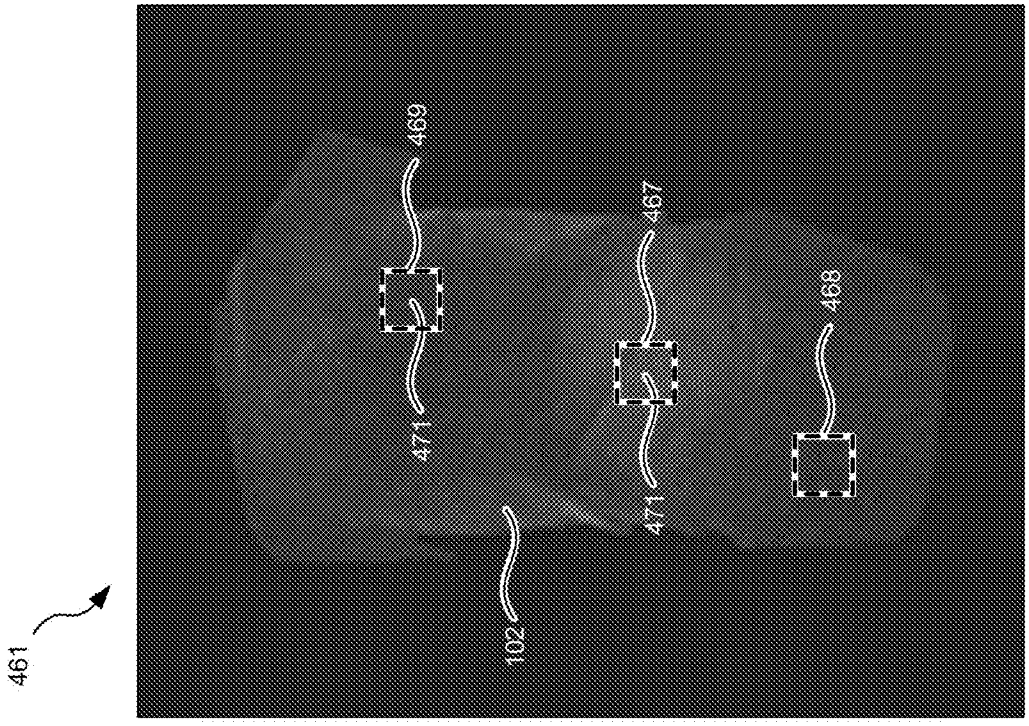
FIGS. 4A-4C are schematic views of images of a region of interest generated from images captured using an image capture device of a video-based patient monitoring system configured in accordance with various embodiments of the present technology.
Figure 4B:
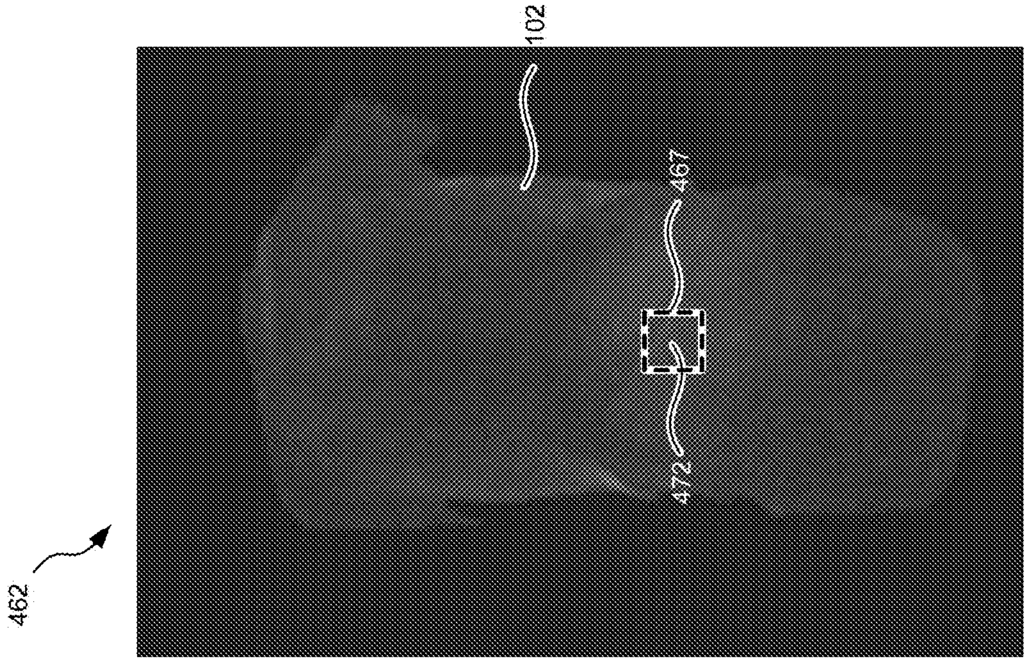
Figure 4C:
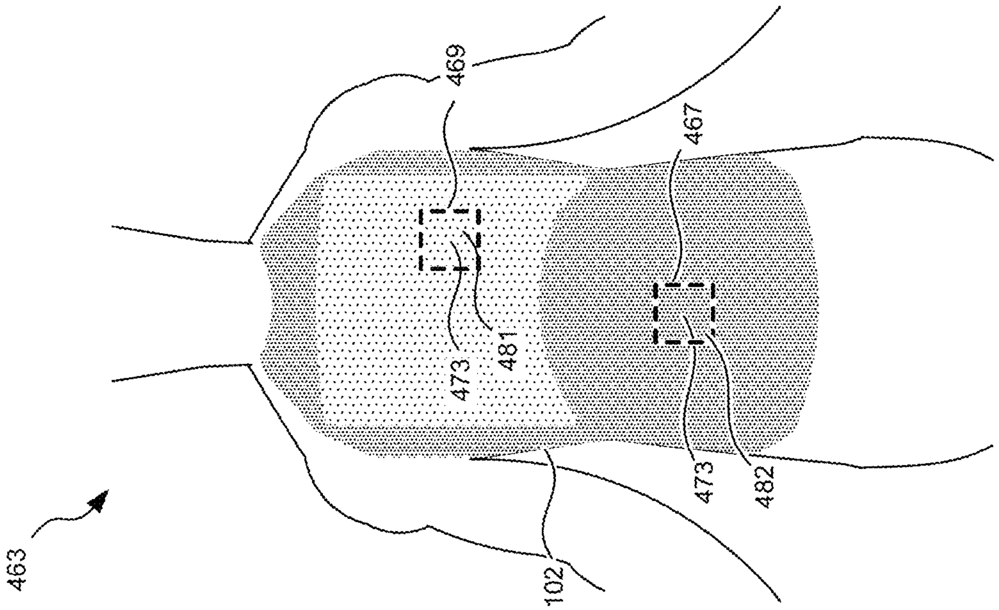

FIGS. 4A-4C are schematic views of images 461-463, respectively, of an aggregate ROI 102. The images 461-463 can be generated from images of the ROI 102 captured using an image capture device of a video-based patient monitoring system configured in accordance with various embodiments of the present technology. In some embodiments, the video-based patient monitoring system can capture images of the ROI 102 by directing the image capture device toward the ROI 102 and capturing a sequence of two or more images (e.g., a video sequence) of the ROI 102. As described in greater detail below, the generated images 461 and 463 illustrate outward movement (e.g., in real-time) of a patient's torso within the ROI 102, whereas the generated image 462 illustrates inward movement (e.g., in real-time) of the patient's torso within the ROI 102.

Using two images of the two or more captured images, the system can calculate change(s) in depth over time between the image capture device and one or more regions (e.g., one or more pixels or groups of pixels) within a ROI. For example, the system can compute a difference between a first depth of a first region 467 in the ROI 102 in image 461 (a first image of the two or more captured images) and a second depth of the first region 467 in the ROI 102 in image 462 (a second image of the two or more captured images). With these differences in depth, the system can determine if a region is moving toward the camera or away from the camera. In some embodiments, the system can assign visual indicators (e.g., colors, patterns, shades, concentrations, intensities, etc.) from a predetermined visual scheme to regions in an ROI based on their movement. The visual indicators can correspond to changes in depth computed by the system (e.g., to the signs and/or magnitudes of computed changes in depth). As shown in FIGS. 4A and 4B, for example, the system can assign (i) a first color 471 (e.g., green) to regions (e.g., to regions 467 and 469 in the image 461) in the ROI 102 that the system determines have moved toward the image capture device over time (e.g., that have exhibited negative changes in depth across two captured images), (ii) a second color 472 (e.g., red) to regions (e.g., to region 467 in the image 462) in the ROI 102 that the system determines have moved away from the image capture device over time (e.g., that have exhibited positive changes in depth across two captured images), and/or (iii) no color or a third color (e.g., black, blue, or yellow) to regions (e.g., to region 468 in the image 461) in the ROI 102 that the system determines have not moved toward or away from the image capture device over time (e.g., that have exhibited negligible changes in depth and/or changes in depth equivalent to zero across two images). In these and other embodiments, the system can assign a fourth color (e.g., black, blue, or yellow) or no color to regions that exhibit changes in depth that the system determines are not physiological and/or are not related to respiratory motion (e.g., changes in depth that are too quick, changes in depth indicative of gross body movement, changes in depth due to noise, etc.) and/or to regions outside of the ROI 102.

In these and other embodiments, the shade of the assigned colors can be positively correlated with the magnitude of a computed change in depth. As shown in FIG. 4A, for example, the shade of the first color 471 assigned to the region 467 in the image 461 is much lighter than the shade of the first color 471 assigned to the region 469. This is because the portion of the patient's body that corresponds to the region 467 in the image 461 exhibited a greater change in depth (moved a greater distance toward the image capture device) over time than the portion of the patient's body that corresponds to the region 469 in the image 461 (which also moved toward the image capture device, as indicated by the green color, but by a lesser distance). In this manner, the visual indicators assigned to regions within the ROI 102 vary spatially within the images 461 and 462.

Although the visual indicators displayed in the images 461 and 462 illustrated in FIGS. 4A and 4B, respectively, are colors with varying shades, video-based patient monitoring systems configured in accordance with other embodiments of the present technology can use other visual indicators, such as patterns, grayscale shades, intensities, concentrations, and/or densities, to visually depict changes in depth over time. For example, a video-based patient monitoring system can assign (i) a first pattern to regions in the ROI that the system determines have moved toward the image capture device over time (e.g., that have exhibited negative changes in depth across two captured images) and (ii) a second pattern to regions in the ROI that the system determines have moved away from the image capture device over time (e.g., that have exhibited positive changes in depth across two captured images). In some embodiments, the system can assign a third pattern or no pattern to (a) regions in the ROI that the system determines have not changed in depth toward or away from the image capture device over time (e.g., that have exhibited negligible changes in depth and/or changes in depth equivalent to zero across two images); (b) regions in the ROI that the system determines are not physiological and/or are not related to respiratory motion (e.g., changes in depth that are too quick, changes in depth indicative of gross body movement, changes in depth due to noise, etc.); and/or (c) regions outside of the ROI 102.

In these and other embodiments, the concentration (e.g., the density) of an assigned pattern can be relative to an amount of excursion of a region in an ROI over time. For example, as shown in image 463 illustrated in FIG. 4C, the concentration of an assigned pattern can be positively correlated with a magnitude of a computed change in depth. In these embodiments, the system (i) can assign a first pattern 473 with a first concentration 481 (for example, a speckled pattern with a first number of dots per area) to the region 469 that the system determined has exhibited a change in depth over time having a first magnitude and (ii) can assign the first pattern 473 with a second concentration 482 (for example, the same speckled pattern but with a second, higher number of dots per area) to the region 467 that the system determined has exhibited a change in depth over time having a second magnitude greater than the first magnitude. As a result, regions in the ROI with no detected change in depth (e.g., a negligible change in depth and/or a change in depth equivalent to zero) can be displayed with a third pattern and/or appear as if no visual indicator has been assigned to these regions (e.g., without a pattern). In some embodiments, regions outside of the ROI can be displayed with a fourth pattern and/or appear as if no visual indicator has been assigned to these regions (e.g., without a pattern).

As a result, a user (e.g., a clinician, nurse, etc.) of the system is able to quickly and easily determine a number of patient breathing characteristics of a patient based on displayed visual indicators. For example, a user is able to quickly and easily determine that a patient is breathing (based on the presence of visual indicators displayed) and whether the patient is currently inhaling or exhaling (based on the particular visual indicators displayed). In addition, a user and/or the system is able to quickly and easily detect one or more breathing abnormalities. For example, the user and/or the system can determine that a patient is currently experiencing paradoxical breathing (e.g., when the chest and abdomen are moving in opposite directions) based on the difference in visual indicators displayed over the patient's chest and abdomen. As another example, the user and/or the system can determine whether a patient is straining to breathe based on the presence of visual indicators on a patient's neck or based on characteristics of visual indicators (e.g., low intensity, low concentration, no visual indicators displayed, etc.) displayed over specific regions (e.g., the abdomen) of the patient.

Figure 5B:
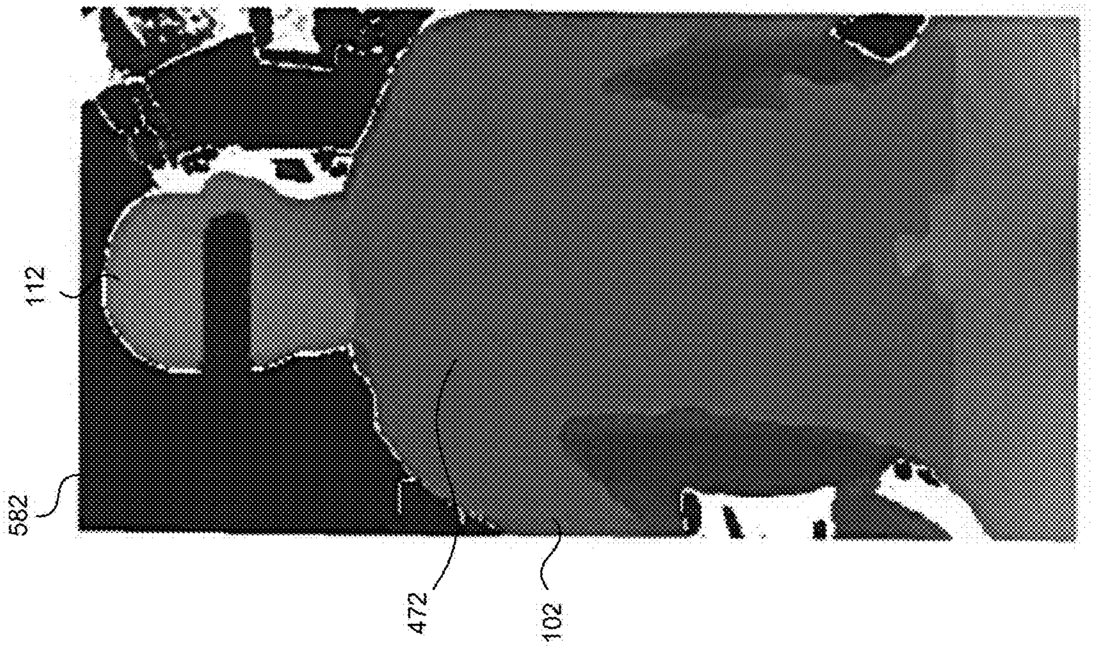
FIGS. 5A and 5B are schematic views of images of a region of interest generated from images captured using an image capture device of a video-based patient monitoring system configured in accordance with various embodiments of the present technology.
Figure 5A:
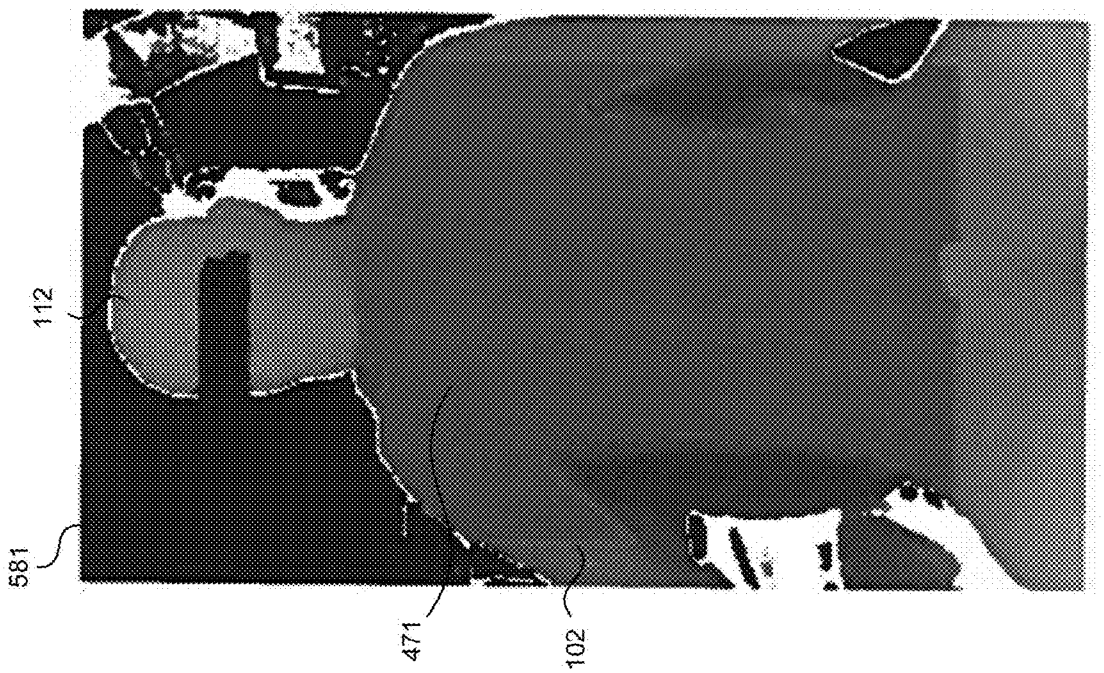

FIGS. 5A and 5B are schematic views of images 581 and 582, respectively, of the aggregate ROI 102. The images 581 and 582 can be generated from images of the ROI 102 captured using an image capture device of a video-based patient monitoring system configured in accordance with various embodiments of the present technology and in a manner similar to the images 461 and/or 462 illustrated in FIGS. 4A and 4B. Also, similar to the visual indicators illustrated in the images 461 and/or 462, the visual indicators illustrated in the images 581 and 582 can correspond to changes in depth computed by the system (e.g., to the signs and/or magnitudes of computed changes in depth).

The images 581 and 582 differ from the images 461 and/or 462, however, in that the aggregate ROI 102 is displayed with spatially uniform visual indicators across the ROI 102. As shown in FIGS. 5A and 5B, for example, the system can assign and/or display (i) the same intensity of the first color 471 to all regions in the aggregate ROI 102 (as shown in the image 581) when the system determines that an average displacement of the regions in the ROI 102 is negative (e.g., that the average displacement of the regions in the ROI 102 is toward the image capture device over time), and/or (ii) the same intensity of the second color 472 to all regions in the aggregate ROI 102 (as shown in the image 582) when the system determines that an average displacement of the regions in the ROI 102 is positive (e.g., that the average displacement of the regions in the ROI 102 is away from the image capture device over time). In some embodiments, the system can determine an average displacement of the ROI 102 by integrating depth changes across all regions in the ROI 102 over two or more images in a captured video sequence. In some embodiments, the intensity of the first color 471 and/or the intensity of the second color 472 assigned to and displayed across all regions in the aggregate ROI 102 can be a predetermined intensity from a predetermined visual scheme. In other embodiments, the intensity of the first color 471 and/or the intensity of the second color 472 can be (i) an average instantaneous intensity relative to an average amount of excursion of all regions in the ROI 102 over two images of the video sequence, or (ii) an average intensity relative to an average amount of excursion of all regions in the ROI 102 over time (e.g., a predetermined number of images in the video sequence). In some embodiments, the system can assign and/or display the same intensity of a third color (e.g., black, blue, or yellow) to (a) regions in the images 581 and/or 582 that the system determines have not changed in depth toward or away from the image capture device over time (e.g., that have exhibited negligible changes in depth and/or changes in depth equivalent to zero across two images); (b) regions in the images 581 and/or 582 that the system determines are not physiological and/or are not related to respiratory motion (e.g., changes in depth that are too quick, changes in depth indicative of gross body movement, etc.); and/or (c) regions in the images 581 and/or 582 outside of the ROI 102.

In other embodiments, the system can assign and/or display visual indicators based on displacement of a majority of the regions in the ROI 102. For example, the system can assign and/or display the same intensity of the first color 471 to all regions in the aggregate ROI 102 when the system determines that a majority of the regions in the ROI 102 have moved toward the image capture device over time (e.g., that a majority of the regions in the ROI 102 have exhibited negative changes in depth across two capture images). In these and other embodiments, the system can assign and/or display the same intensity of the second color 472 to all regions in the aggregate ROI 102 when the system determines that a majority of the regions in the ROI 102 have moved away from the image capture device over time (e.g., that a majority of the regions in the ROI 102 have exhibited positive changes in depth across two capture images).

Regardless of the visual scheme employed, the system can display (e.g., in real-time) the assigned visual indicators over corresponding regions of the ROI in a captured image to visually portray the computed changes in depths. For example, the assigned visual indicators can be displayed within the ROI 102 and overlaid onto a depth image (e.g., a 3-D representation of a surface, including point clouds, iso-surfaces (contours), wire frames, etc.), an RGB image, and infrared image, an MRI image, and/or CT image of the patient 112, among other image types of the patient 112. Thus, the assigned visual indicators can exaggerate or emphasize changes in depths detected by the system. In turn, a user (e.g., a caregiver, a clinician, a patient, etc.) can quickly and easily determine whether or not a patient 112 is breathing based on whether or not the colors get brighter, or the patterns get darker/denser, during a breath (that is, based on whether or not the visual indicators displayed on the ROI 102 correspond to one or more breathing cycles of the patient 112).

Additionally or alternatively, a user can quickly and easily determine a phase (e.g., inhalation and/or exhalation) of a patient's breathing. For example, a large majority of the ROI 102 in the generated image 461 illustrated in FIG. 4A and all of the ROI 102 in the generated image 581 illustrated in FIG. 5A depict the first color 471 (in this example, green). As discussed above, the first color 471 corresponds to negative changes in depths computed by the system—movements toward the camera. In other words, the generated images 461 and 581 illustrate that the displacement of the large majority of the ROI 102 and/or the average displacement of the ROI 102 is toward the image capture device of the system and out from the patient's body over time. Based on these displays, a user can quickly and easily determine that the patient 112 is currently inhaling—the patient's chest is expanding toward the camera. Similarly, a large majority of the ROI 102 in the generated image 462 illustrated in FIG. 4B and all of the ROI 102 in the generated image 582 in FIG. 5B depict the second color 472 (in this example, red). As discussed above, the second color 472 corresponds to positive changes in depths computed by the system—movements away from the camera. In other words, the generated images 462 and 582 illustrate that the displacement of the large majority of the ROI 102 and/or the average displacement of the ROI 102 is away from the image capture device of the system and in toward the patient's body over time. Based on these displays, a user can quickly and easily determine that the patient 112 is currently exhaling—the patient's chest is retracting away from the camera.

Figure 6:
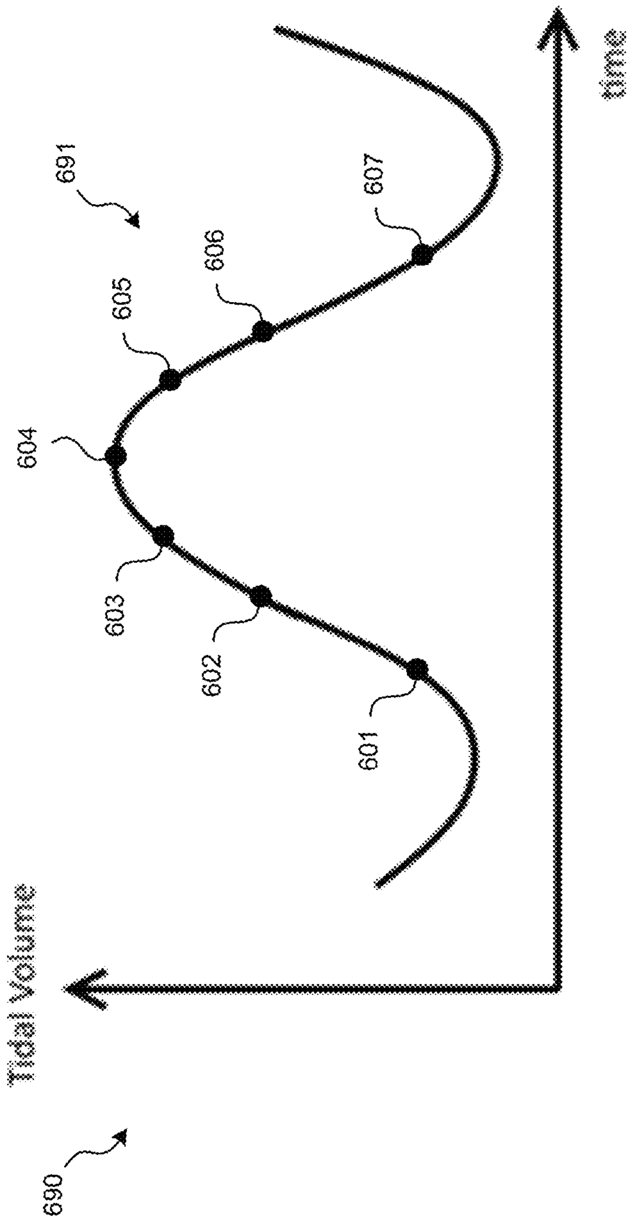
FIG. 6 is a line plot illustrating a tidal volume signal generated using a video-based patient monitoring system configured in accordance with various embodiments of the present technology.
Figures 7A, 7B, 7C, 7D, 7E, 7F:
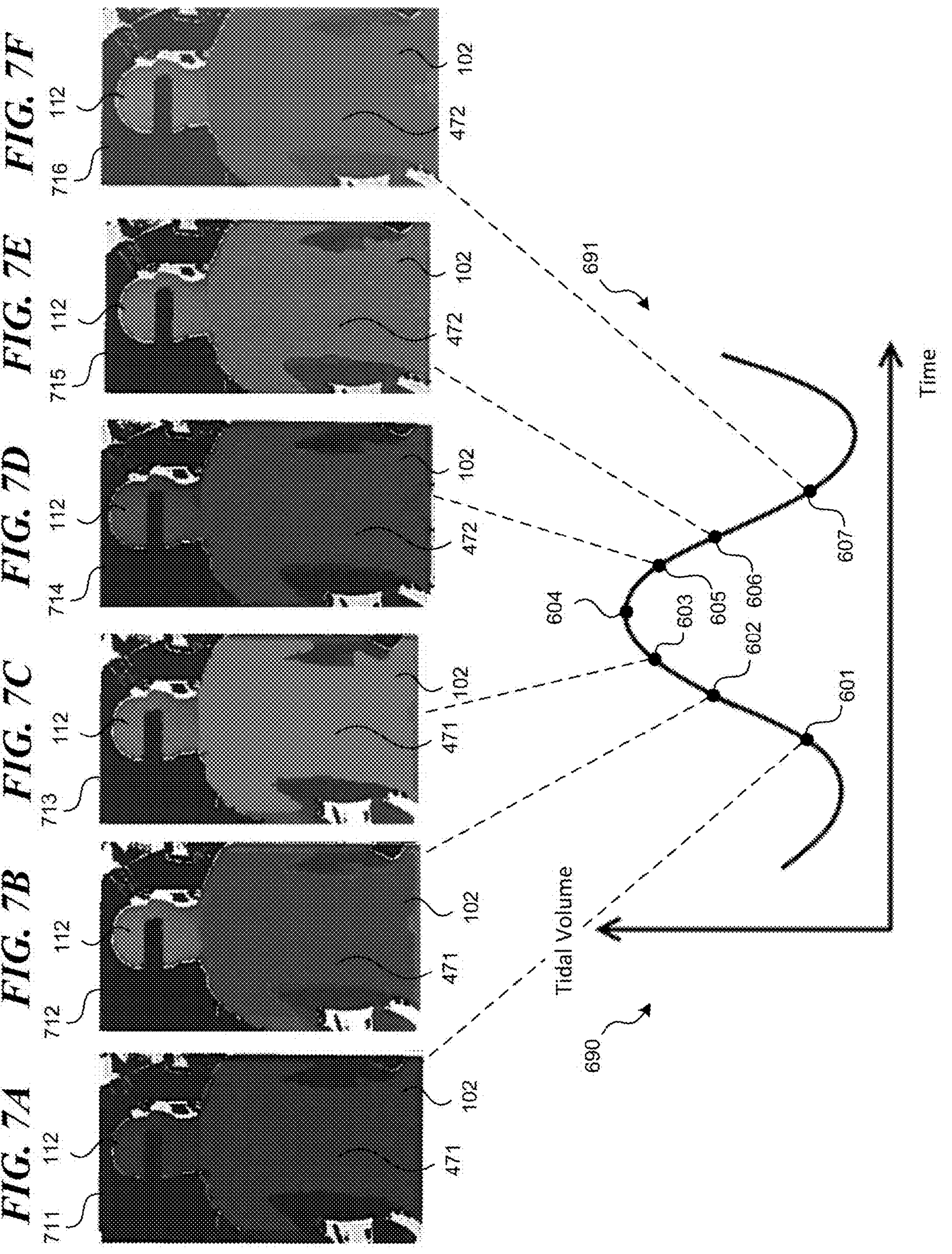
FIGS. 7A-7F are schematic views of images of a region of interest generated from images captured using an image capture device of a video-based patient monitoring system configured in accordance with various embodiments of the present technology.
Figures 8A, 8B, 8C, 8D, 8E, 8F:
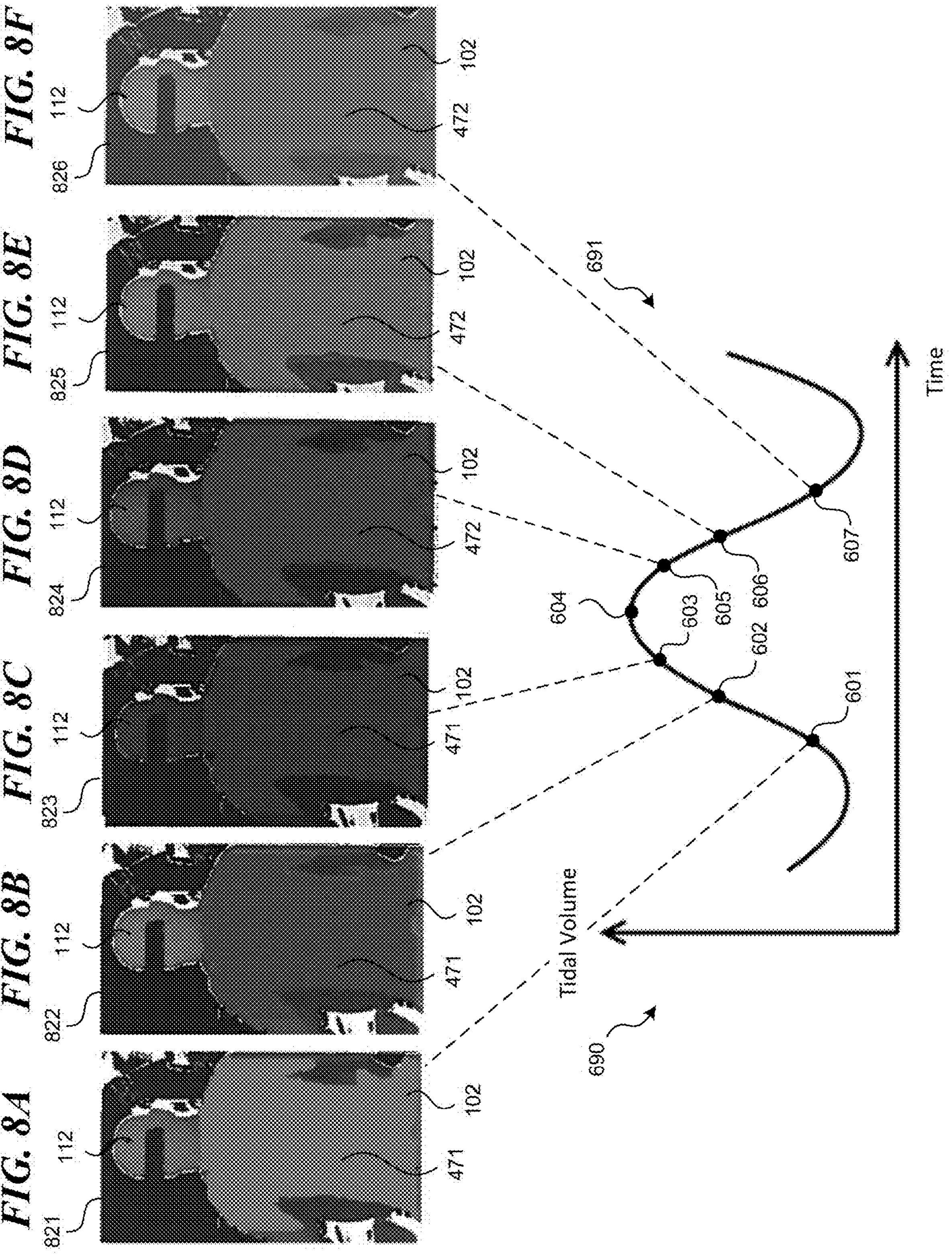
FIGS. 8A-8F are schematic views of images of a region of interest generated from images captured using an image capture device of a video-based patient monitoring system configured in accordance with various embodiments of the present technology.
Figures 9A, 9B, 9C, 9D, 9E, 9F:
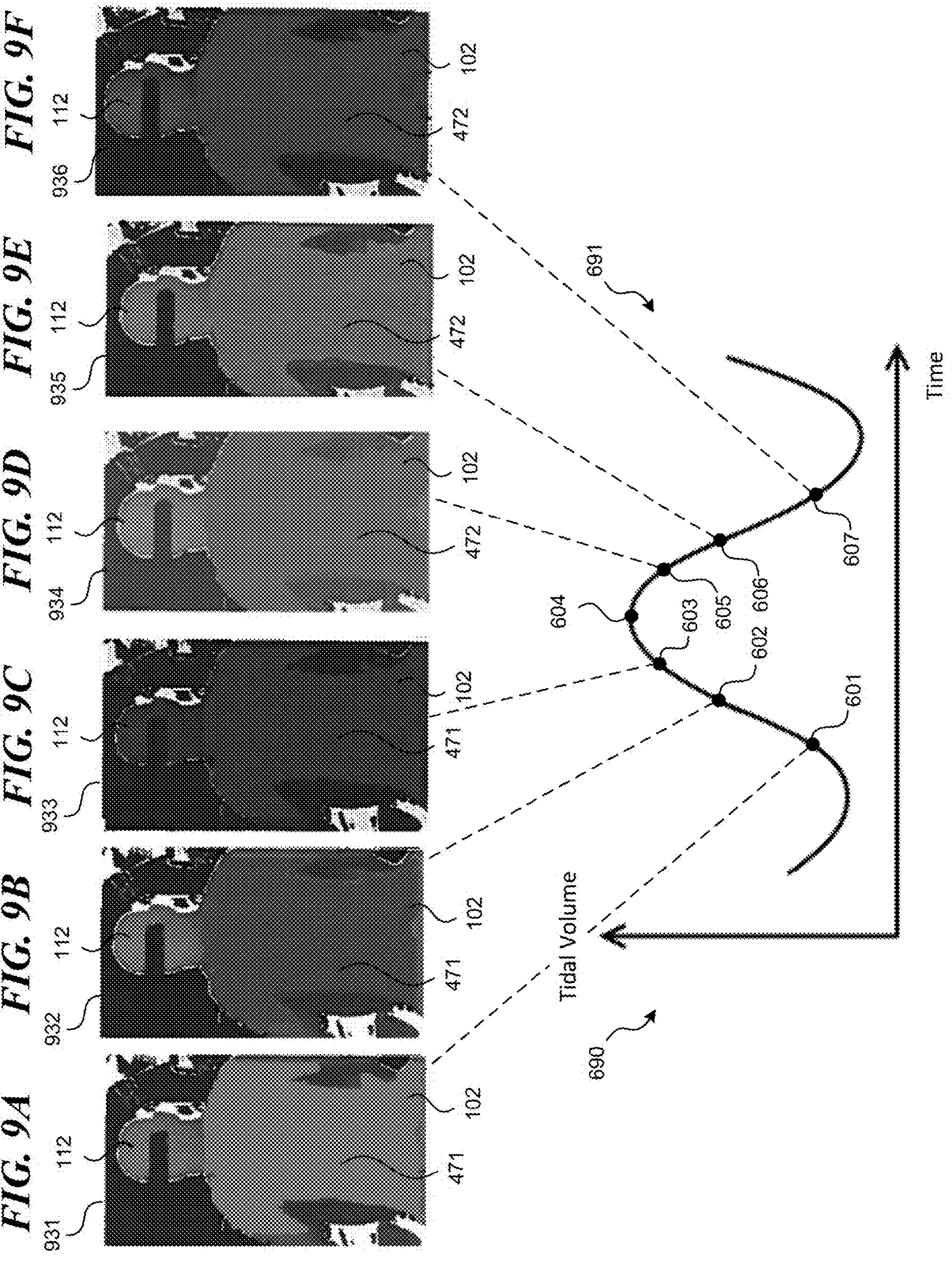
FIGS. 9A-9F are schematic views of images of a region of interest generated from images captured using an image capture device of a video-based patient monitoring system configured in accordance with various embodiments of the present technology.
Figures 10A, 10B, 10C, 10D, 10E, 10F:
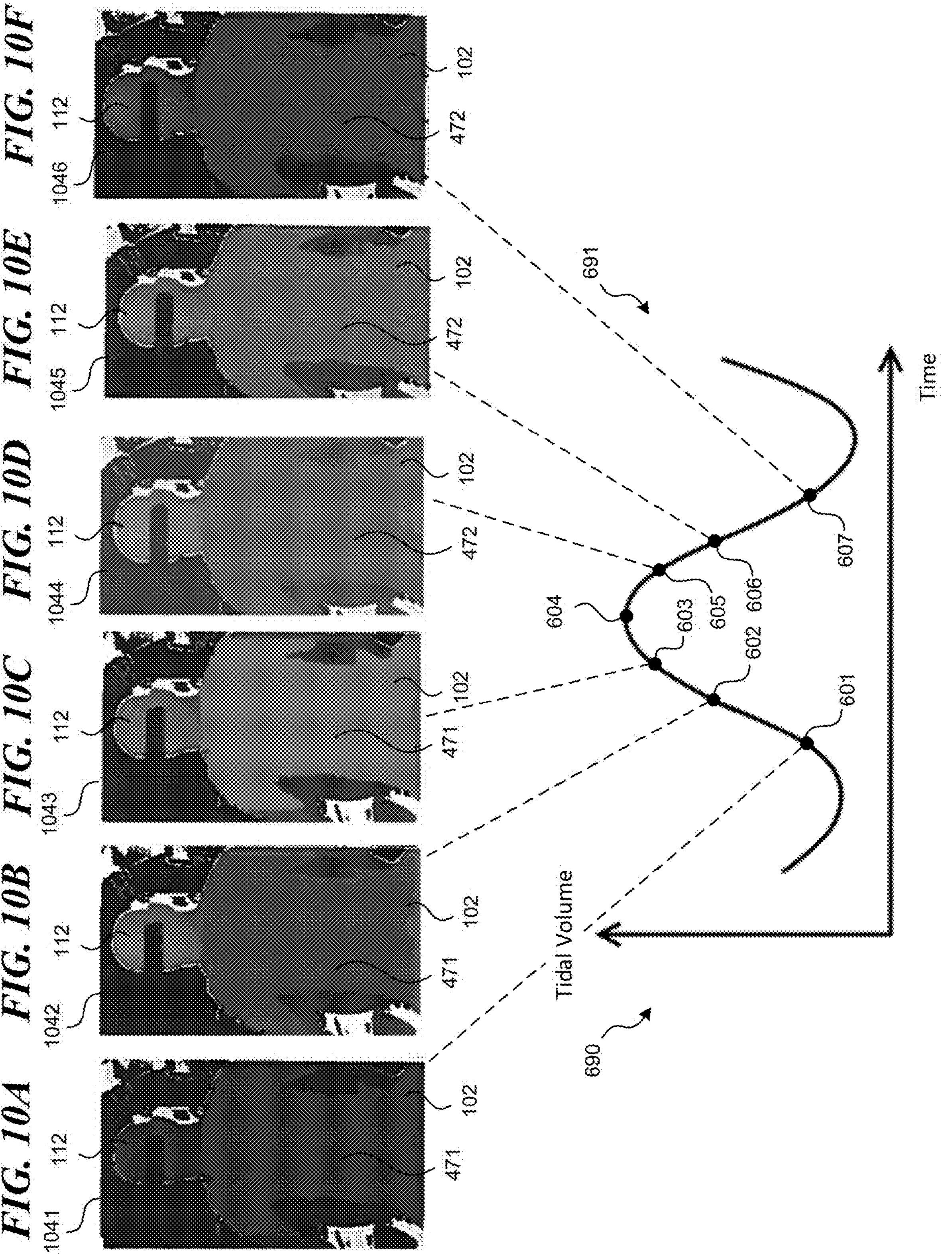
FIGS. 10A-10F are schematic views of images of a region of interest generated from images captured using an image capture device of a video-based patient monitoring system configured in accordance with various embodiments of the present technology.
Figures 11A, 11B, 11C, 11D, 11E, 11F:
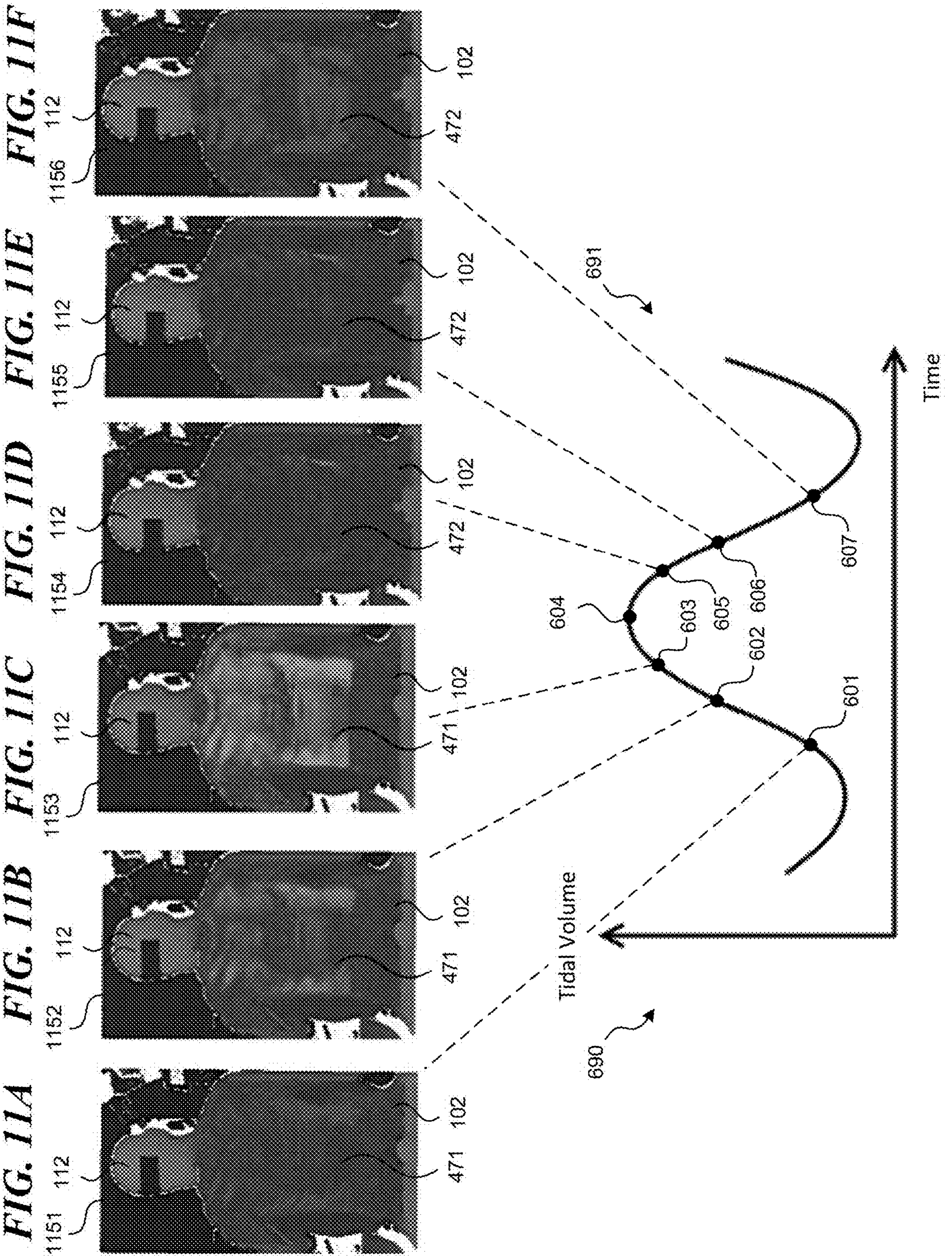
FIGS. 11A-11F are schematic views of images of a region of interest generated from images captured using an image capture device of a video-based patient monitoring system configured in accordance with various embodiments of the present technology.

FIG. 6 is a line plot 690 illustrating a tidal volume signal 691 generated using a video-based patient monitoring system configured in accordance with various embodiments of the present technology. In some embodiments, the system can generate the tidal volume signal 691 by (e.g., continuously) integrating all volume changes computed across an aggregate ROI 102 on a patient 112. The tidal volume signal 691 can provide an indication of the volume of air displaced by a patient 112 between inhalation and exhalation. In these and other embodiments, the video-based patient monitoring system can use the tidal volume signal 691 to determine one or more parameters of a patient's breathing, such as respiration rate, inhalation-to-exhalation ratio, respiratory minute volume, and others.

As shown in FIG. 6, the line plot 690 includes several points 601-607 along the tidal volume signal 691 at various positions within one cycle of a patient's breathing. For example, points 601-604 are positioned along an inhalation portion of the patient's breathing cycle, and points 604-607 are positioned along an exhalation portion of the patient's breathing cycle. As discussed above and in greater detail below, the system can provide a clinician a visualization of a patient's breathing by, for example, overlaying an ROI (e.g., the aggregate ROI 102) onto a display (e.g., an image and/or video sequence) of the patient 112 while simultaneously displaying visual indicators assigned to regions within the ROI 102. In some embodiments, the system can display the visualization in real-time such that the current display corresponds to a current position within the patient's breathing cycle. In other words, the display can change throughout a patient's breathing cycle to depict whether the patient 112 is, for example, inhaling, exhaling, beginning to inhale or exhale, finishing inhaling or exhaling, etc. For example, the system can display a constant intensity of the first color 471 (e.g., as shown in the generated image 581 illustrated in FIG. 5A) while the patient 112 is inhaling (e.g., at points 601-604 along the tidal volume signal 691). In these and other embodiments, the system can display a constant intensity of the second color 472 (e.g., as shown in the generated image 582 illustrated in FIG. 5B) while the patient 112 is exhaling (e.g., at points 604-607 along the tidal volume signal 691). In some embodiments, the first color 471 and/or the second color 472 can be displayed across all regions within the ROI 102 overlaid onto the patient 112. In other embodiments, the first color 471 and/or the second color 472 can be displayed only on regions within the ROI 102 that experience excursion in a direction corresponding to the current phase (inhalation or exhalation) of the patient's breathing. As such, a user of the system can quickly and easily determine when the patient 112 is breathing, when the patient 112 is inhaling, and/or when the patient 112 is exhaling based on the visualization of the patient's breathing cycle displayed by the system (e.g., based on the presence of visual indicators overlaid onto the patient 112 and/or on the particular visual indications displayed).

In some embodiments, the visual indicators overlaid onto the patient 112 can vary along the inhalation portion and/or the exhalation portion of the patient's breathing. For example, FIGS. 7A-10F are schematic views of images 711-716, 821-826, 931-936, and 1041-1046, respectively, of the aggregate ROI 102. The images 711-716, 821-826, 931-936, and 1041-1046 can be generated from images of the ROI 102 captured using an image capture device of a video-based patient monitoring system configured in accordance with various embodiments of the present technology and in a manner similar to the images 461, 462, 463, 581, and/or 582 (FIGS. 4A, 4B, 4C, 5A, and 5B, respectively). Also similar to the visual indicators illustrated in the images 461, 462, 463, 581, and/or 582, the visual indicators illustrated in the images 711-716, 821-826, 931-936, and 1041-1046 can correspond to changes in depth computed by the system (e.g., to the signs and/or magnitudes of computed changes in depth).

The intensities of the visual indicators displayed across all regions in the ROI 102 in the images 711-716, 821-826, 931-936, and 1041-1046 correspond to a position along the patient's breathing cycle. In some embodiments, the system can display the first color 471 across all regions in the ROI 102 while the patient 112 is inhaling, and the intensity of the first color 471 displayed within the ROI 102 can increase as the tidal volume signal 691 (FIG. 6) increases. For example, the system can display the image 711 (FIG. 7A) at point 601 along the tidal volume signal 691, can display the image 712 (FIG. 7B) at point 602 along the tidal volume signal 691, and can display the image 713 (FIG. 7C) at point 603 along the tidal volume signal 691. The intensity of the first color 471 in the image 712 is greater than the intensity of the first color 471 in the image 711, and the intensity of the first color 471 in the image 713 is greater than the intensities of the first color 471 in the images 711 and 712. As a result, a user viewing the sequence of the images 711-713 can quickly and easily determine that the patient 112 is breathing (indicated by the presence of a visual indicator overlaid onto the patient 112 within the ROI 102), is currently inhaling (indicated by the presence of the first color 471), and is nearing the end of the inhalation portion of the patient's breathing cycle (indicated by the high intensity of the first color 471 within the image 713).

In these and other embodiments, the system can display the second color 472 across all regions in the ROI 102 while the patient 112 is exhaling, and the intensity of the second color 472 displayed within the ROI 102 can increase as the tidal volume signal 691 decreases. For example, the system can display the image 714 (FIG. 7D) at point 605 along the tidal volume signal 691 (FIG. 6), display the image 715 (FIG. 7E) at point 606 along the tidal volume signal 691, and display the image 716 (FIG. 7E) at point 607 along the tidal volume signal 691. The intensity of the second color 472 in the image 715 is greater than the intensity of the second color 472 in the image 715, and the intensity of the second color 472 in the image 716 is greater than the intensities of the second color 472 in the images 714 and 715. As a result, a user viewing the sequence of the images 714-716 can quickly and easily determine that the patient 112 is breathing (indicated by the presence of a visual indicator within the ROI 102), is currently exhaling (indicated by the presence of the second color 472), and is nearing the end of the exhalation portion of the patient's breathing cycle (indicated by the high intensity of the second color 472 within the image 716).

In FIGS. 7A-7F, both colors increase in brightness as the breath continues (the green color gets brighter as the patient breathes in, and the red color gets brighter as the patient breathes out). Either of these can be reversed, so that colors get brighter or darker as the patient breathes in or out. For example, in other embodiments, the intensity of the first color 471 displayed within the ROI 102 can decrease as the tidal volume signal 691 increases (green gets darker as the patient breathes in), and/or the intensity of the second color 472 displayed within the ROI 102 can decrease as the tidal volume signal 691 decreases (red gets darker as the patient breathes out). FIGS. 8A-10F illustrate some of these alternative embodiments. Referring to FIGS. 8A-8F, for example, the system can display the image 821 (FIG. 8A) at point 601 along the tidal volume signal 691 (FIG. 6); display the image 822 (FIG. 8B) at point 602 along the tidal volume signal 691; display the image 823 (FIG. 8C) at point 603 along the tidal volume signal 691; display the image 824 (FIG. 8D) at point 605 along the tidal volume signal 691; display the image 825 (FIG. 8E) at point 606 along the tidal volume signal 691; and/or display the image 826 (FIG. 8F) at point 607 along the tidal volume signal 691. In FIGS. 8A-8F, the intensity of the first color 471 can decrease as the tidal volume signal 691 increases, and the intensity of the second color 472 can increase as the tidal volume signal 691 decreases. Referring to FIGS. 9A-9F, the system can display the image 931 (FIG. 9A) at point 601 along the tidal volume signal 691; display the image 932 (FIG. 9B) at point 602 along the tidal volume signal 691; display the image 933 (FIG. 9C) at point 603 along the tidal volume signal 691; display the image 934 (FIG. 9D) at point 605 along the tidal volume signal 691; display the image 935 (FIG. 9E) at point 606 along the tidal volume signal 691; and/or display the image 936 (FIG. 9F) at point 607 along the tidal volume signal 691. In these embodiments, the intensity of the first color 471 can decrease as the tidal volume signal 691 increases, and the intensity of the second color 472 can decrease as the tidal volume signal 691 decreases. Finally, referring to FIGS. 10A-10F, the system can display the image 1041 (FIG. 10A) at point 601 along the tidal volume signal 691; display the image 1042 (FIG. 10B) at point 602 along the tidal volume signal 691; display the image 1043 (FIG. 10C) at point 603 along the tidal volume signal 691; display the image 1044 (FIG. 10D) at point 605 along the tidal volume signal 691; display the image 1045 (FIG. 10E) at point 606 along the tidal volume signal 691; and/or display the image 1046 (FIG. 10F) at point 607 along the tidal volume signal 691. In these embodiments, the intensity of the first color 471 can increase as the tidal volume signal 691 increases, and the intensity of the second color 472 can decrease as the tidal volume signal 691 decreases.

Although the generated images 711-716, 821-826, 931-936, and 1041-1046 (FIGS. 7A-10F) are illustrated with spatially uniform visual indicators (in this case, a uniform color) across all regions in the ROI 102, the visual indicators in other embodiments can spatially vary across the regions of the ROI 102 (e.g., by using various shades of the first color 471 and/or the second color 472). For example, FIGS. 11A-11F are schematic views of images 1151-1156, respectively, of the aggregate ROI 102. The images 1151-1156 can be generated from images of the ROI 102 captured using an image capture device of a video-based patient monitoring system configured in accordance with various embodiments of the present technology and in a manner similar to the images 461, 462, 463, 581, 582, 711-716, 821-826, 931-936, and/or 1041-1046 illustrated in FIGS. 4A-5B and 7A-10F, respectively. Also similar to the visual indicators illustrated in the images 461, 462, 463, 581, 582, 711-716, 821-826, 931-936, and/or 1041-1046, the visual indicators illustrated in the images 1151-1156 can correspond to changes in depth computed by the system (e.g., to the signs and/or magnitudes of computed changes in depth). In some embodiments, the system can display the image 1151 (FIG. 11A) at point 601 along the tidal volume signal 691 (FIG. 6); display the image 1152 (FIG. 11B) at point 602 along the tidal volume signal 691; display the image 1153 (FIG. 11C) at point 603 along the tidal volume signal 691; display the image 1154 (FIG. 11D) at point 605 along the tidal volume signal 691; display the image 1155 (FIG. 11E) at point 606 along the tidal volume signal 691; and/or display the image 1156 (FIG. 11F) at point 607 along the tidal volume signal 691. In these embodiments, similar to the embodiment illustrated in FIGS. 7A-7F, the intensity of the first color 471 can increase as the tidal volume signal 691 increases, and the intensity of the second color 472 can increase as the tidal volume signal 691 decreases. In contrast with the embodiment illustrated in FIGS. 7A-7F, however, the visual indicators displayed within the ROI 102 in the embodiment illustrated in FIGS. 11A-11F spatially vary such that the system provides a user an indication of the amount of excursion a particular region within the ROI 102 experienced over time (e.g., whether the particular region of the patient's chest is moving and by how much) in addition to (i) an indication that the patient 112 is breathing, (ii) an indication of the current phase (e.g., inhalation or exhalation) of the patient's breathing, and/or (iii) an indication of the current position of the patient's breathing within the patient's breathing cycle.

Another approach for visually representing a patient's breathing cycle, based on images captured with a depth sensing camera, is shown in FIGS. 12A-12C and 13A-13C. These figures are schematic views of images 1261-1263 and 1371-1373, respectively, of an aggregate ROI 102 generated from images captured using an image capture device of a video-based patient monitoring system. The images 1261-1263 and 1371-1373 can be generated from images of the ROI 102 captured using an image capture device of a video-based patient monitoring system configured in accordance with various embodiments of the present technology and in a manner similar to the images 461, 462, 463, 581, 582, 711-716, 821-826, 931-936, 1041-1046, and/or 1141-1146 illustrated in FIGS. 4A-5B and 7A-11F, respectively. Also similar to the visual indicators illustrated in the images 461, 462, 463, 581, 582, 711-716, 821-826, 931-936, 1041-1046, and/or 1141-1146, the visual indicators illustrated in the images 1261-1263 and 1371-1373 can correspond to changes in depth computed by the system (e.g., to the signs and/or magnitudes of computed changes in depth).

Figures 12A, 12B, 12C, 13A, 13B, 13C:
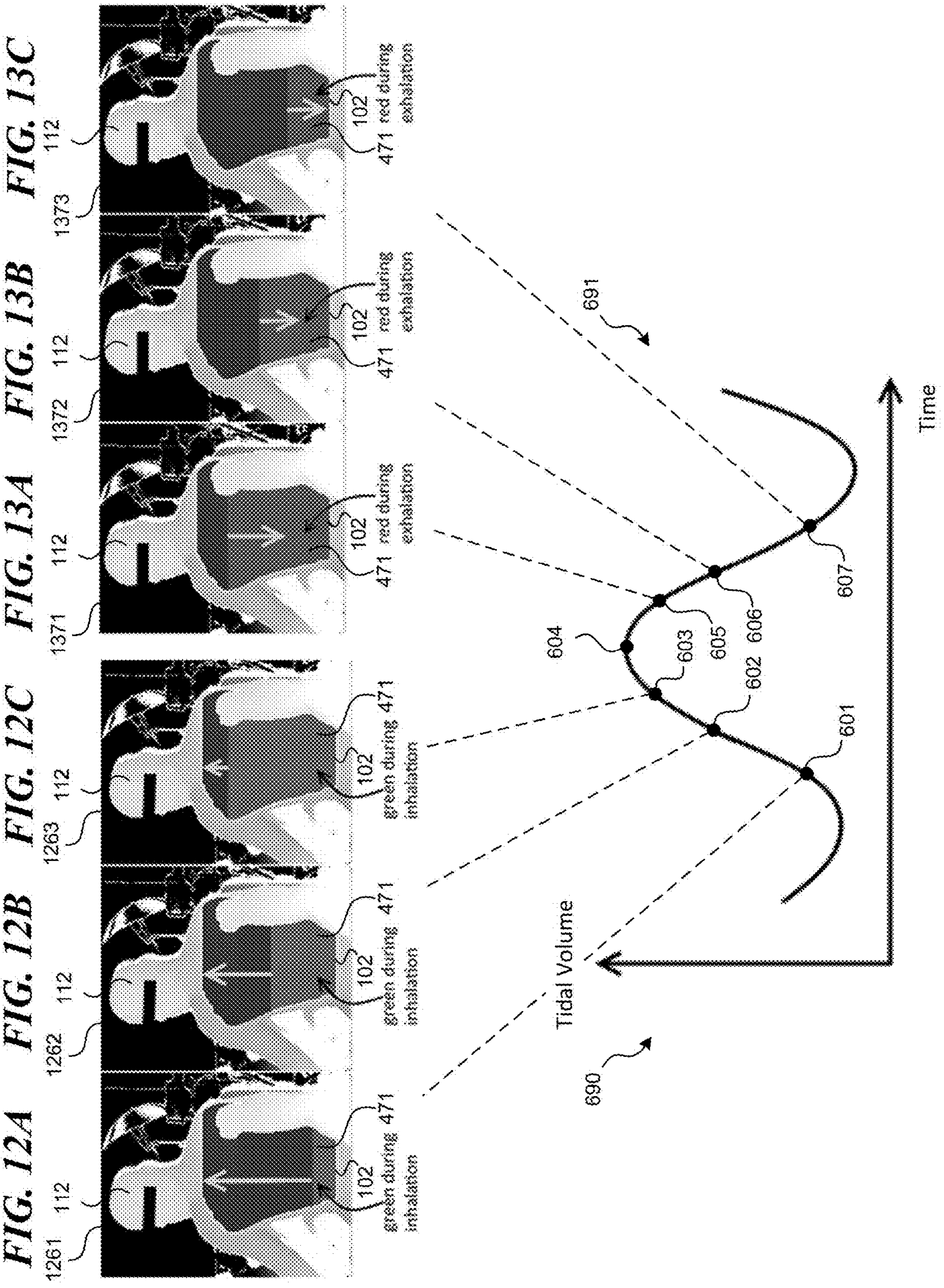
FIGS. 12A-12C are schematic views of images of a region of interest generated from images captured using an image capture device of a video-based patient monitoring system configured in accordance with various embodiments of the present technology.
FIGS. 13A-13C are schematic views of images of a region of interest generated from images captured using an image capture device of a video-based patient monitoring system configured in accordance with various embodiments of the present technology.

The images 1261-1263 and 1371-1373 differ from the images 461, 462, 463, 581, 582, 711-716, 821-826, 931-936, 1041-1046, and/or 1141-1146, however, in that amount (e.g., area) of the ROI 102 filled with one or more visual indicators corresponds to a position along the patient's breathing cycle and/or to an amount (e.g., volume) of air within the patient's lungs. Referring to FIGS. 12A-12C, for example, the system can display the first color 471 in the ROI 102 while the patient 112 is inhaling, and the amount of the ROI 102 filled with the first color 471 can increase as the tidal volume signal 691 (FIG. 6) increases. For example, the system can display the image 1261 (FIG. 12A) at point 601 along the tidal volume signal 691, display the image 1262 (FIG. 12B) at point 602 along the tidal volume signal 691, and display the image 1263 (FIG. 12C) at point 603 along the tidal volume signal 691. The amount of the ROI 102 filled with the first color 471 in the image 1263 is greater than the amount of the ROI 102 filled with the first color 471 in the images 1261 and 1262. Similarly, the amount of the ROI 102 filled with the first color 471 in the image 1262 is greater than the amount of the ROI 102 filled with the first color 471 in the image 1261. As a result, a user viewing the sequence of images 1261-1263 can quickly and easily determine that the patient 112 is breathing (indicated by the presence of a visual indicator, in this case a solid color and an arrow) and is currently inhaling (indicated by the presence of the first color 471, in this case green, and the up arrow). Furthermore, based on the amount of the ROI 102 filled by the first color 471, the system can provide the user an indication of the current position of the patient's breathing within the patient's breathing cycle and/or an indication of the amount (e.g., volume) of air within the patient's lungs. In other embodiments, the amount of the ROI 102 filled with the first color 471 can decrease as the tidal volume signal 691 increases (e.g., the amount of the ROI 102 filled with the first color 471 can be inversely related to or negatively correlated with the inhalation portion of the tidal volume signal 691).

Referring to FIGS. 13A-13C, the system can additionally or alternatively display the second color 472 in the ROI 102 while the patient 112 is exhaling, and the amount of the ROI 102 filled with the second color 472 can decrease as the tidal volume signal 691 (FIG. 6) decreases. For example, the system can display the image 1371 (FIG. 13A) at point 605 along the tidal volume signal 691, display the image 1372 (FIG. 13B) at point 606 along the tidal volume signal 691, and display the image 1373 (FIG. 13C) at point 607 along the tidal volume signal 691. The amount of the ROI 102 filled with the second color 472 in the image 1373 is less than the amount of the ROI 102 filled with the second color 472 in the images 1371 and 1372. Similarly, the amount of the ROI 102 filled with the second color 472 in the image 1372 is less than the amount of the ROI 102 filled with the second color 472 in the image 1371. As a result, a user viewing the sequence of images 1371-1373 can quickly and easily determine that the patient 112 is breathing (e.g., indicated by the presence of a visual indicator, in this case a solid color and an arrow) and is currently exhaling (indicated by the presence of the second color 472, in this case red, and the down arrow). Furthermore, based on the amount of the ROI 102 filled by the second color 472, the system can provide the user an indication of the current position of the patient's breathing within the patient's breathing cycle and/or an indication of the amount (e.g., volume) of air within the patient's lungs. In other embodiments, the amount of the ROI 102 filled with the second color 472 increases as the tidal volume signal 691 decreases (e.g., the amount of the ROI 102 filled with the second color 472 can be inversely related to or negatively correlated with the exhalation portion of the tidal volume signal 691).

Although the generated images 1261-1263 and 1371-1373 are illustrated and displayed with an aggregate ROI 102 in FIGS. 12A-13C, images captured, generated, and/or displayed in accordance with other embodiments of the present technology can include additional or alternative graphics. In some embodiments, for example, a graphic of one or more lungs (not shown) can be displayed over or alongside an image of a patient 112. In these embodiments, the amount of the lung-shaped graphic filled with visual indicators (e.g., the first color 471 and/or the second color 472, or patterns or arrows) can correspond to the phase (e.g., inhalation and/or exhalation) of the patient's breathing and/or to the position of the patient's breathing within the patient's breathing cycle. As an example, the system can fill (or empty) the lungs graphic with a green color to provide (i) an indication that the patient 112 is inhaling, (ii) an indication of the position of the patient's breathing within the inhalation portion of the patient's breathing cycle, and/or (iii) an indication of the amount (e.g., volume) of air within the patient's lungs. In these and other embodiments, the system can empty (or fill) the lungs graphic with a red color to provide (i) an indication that the patient 112 is exhaling, (ii) an indication of the position of the patient's breathing within the exhalation portion of the patient's breathing cycle, and/or (iii) an indication of the amount (e.g., volume) of air within the patient's lungs.

Figure 14:
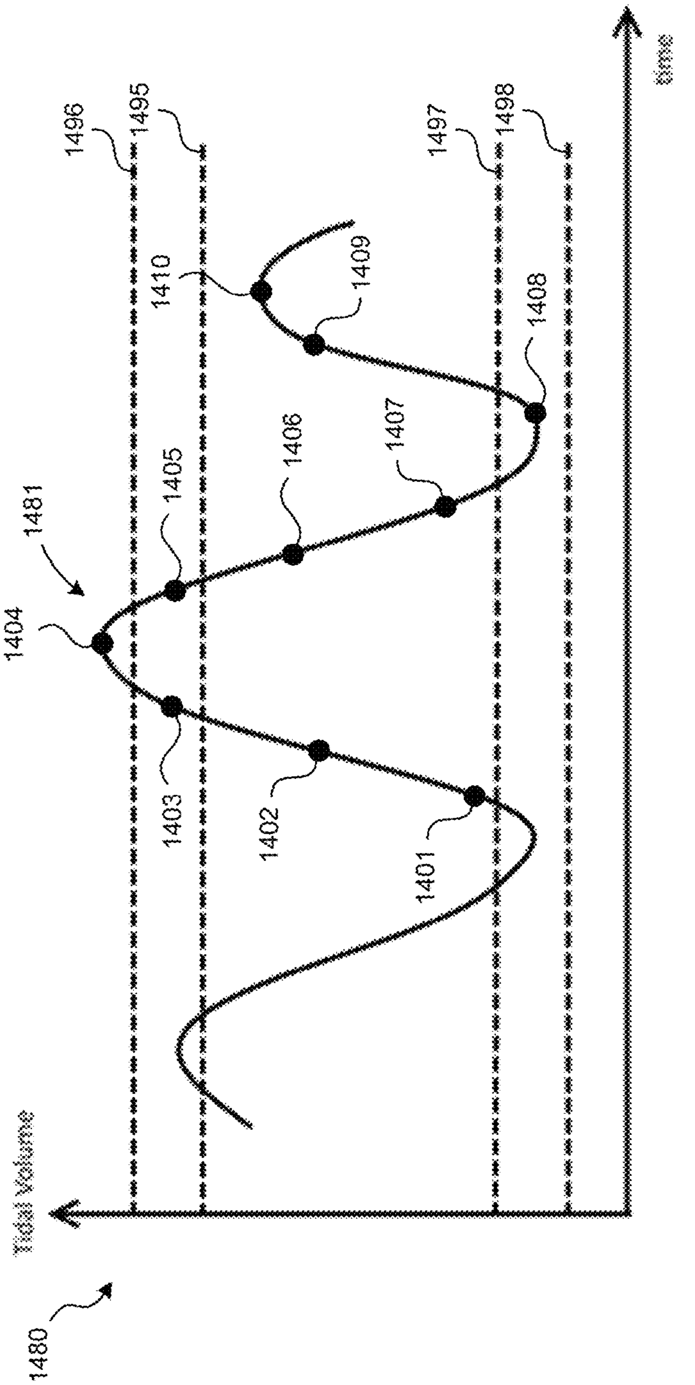
FIG. 14 is a line plot illustrating a tidal volume signal generated using a video-based patient monitoring system configured in accordance with various embodiments of the present technology.

FIG. 14 is a line plot 1480 illustrating a tidal volume signal 1481 generated using a video-based patient monitoring system configured in accordance with various embodiments of the present technology. In some embodiments, the system can generate the tidal volume signal 1481 by (e.g., continuously) integrating all volume changes computed across an aggregate ROI 102 on a patient 112. The tidal volume signal 1481 can provide an indication of the volume of air displaced by a patient 112 between inhalation and exhalation. For example, the amplitude of the tidal volume signal 1481 can provide an indication of the amount (e.g., volume) of air within the patient's lungs. In these and other embodiments, the video-based patient monitoring system can use the tidal volume signal 1481 to determine one or more parameters of a patient's breathing, such as respiration rate, inhalation-to-exhalation ratio, respiratory minute volume, and others.

In some embodiments, a user and/or the system can define one or more inhalation target tidal volumes for a patient 112. As shown in FIG. 14, for example, the line plot 1480 includes an inhalation threshold target tidal volume 1495. The threshold target tidal volume 1495 can be a default threshold target tidal volume (e.g., set automatically by the system). In these and other embodiments, the threshold target tidal volume 1495 can be defined and/or set by a user and/or the system (e.g., by adjusting the default threshold target tidal volume) based on, for example, a patient's demographics, disease state, and/or other factors, such as one or more previous breathing cycles of the patient 112. In some embodiments, the threshold target tidal volume 1495 can represent a target volume of air below which the patient 112 is at risk of hypoventilation, as discussed in greater detail below.

In these and other embodiments, a user and/or the system can define one or more other threshold target tidal volumes in addition to or in lieu of the threshold target tidal volume 1495. For example, a user and/or the system can define a second inhalation threshold tidal volume 1496 (FIG. 14). In some embodiments, the threshold tidal volume 1496 can be defined and/or set by a user and/or the system based on, for example, one or more patient factors. In these and other embodiments, the threshold target tidal volume 1496 can represent a volume of air above which the patient 112 is at risk of hyperventilation, as discussed in greater detail below. In embodiments having both the threshold target tidal volumes 1495 and 1496, the threshold target tidal volumes 1495 and 1496 can be defined and/or set such that they define a range of tidal volumes indicative of normal ventilation for a particular patient 112.

As shown in FIG. 14, a user and/or the system can additionally or alternatively define one or more exhalation threshold target tidal volumes. For example, a user and/or the system can set and/or define exhalation threshold target tidal volumes 1497 and/or 1498 in a manner similar to the inhalation threshold target tidal volumes 1495 and/or 1496 (e.g., based at least in part on one or more patient factors). The threshold target tidal volume 1497 can represent a volume of air used to detect various medical conditions. For example, a user and/or the system can define and/or set the threshold target tidal volume 1497 such that when a patient 112 has difficulty exhaling the air in his/her lungs below the threshold target tidal volume 1497, the patient 112 may be experiencing obstructive lung disease. In these and other embodiments, the second exhalation target tidal volume 1498 can represent a volume of air below which the system can determine the patient 112 is not breathing and/or the patient's breathing is strained, inhibited, restricted, and/or obstructed. In these and still other embodiments, the threshold target tidal volumes 1497 and 1498 can define a range of normal ventilation for a particular patient 112 in a manner similar to the threshold target tidal volumes 1495 and 1496.

The line plot 1480 illustrated in FIG. 14 includes several points 1401-1410 along the tidal volume signal 1481 at various positions along multiple cycles of a patient's breathing. As discussed above and in greater detail below, the system can provide a clinician a visualization of a patient's breathing by, for example, overlaying an ROI (e.g., the aggregate ROI 102) or other graphic (e.g., lungs) onto or alongside a display of the patient 112 while simultaneously displaying visual indicators assigned to regions within the ROI and/or within the graphic.

FIGS. 15A-15D are schematic views of images 1521-1524, respectively, of the aggregate ROI 102. The images 1521-1524 can be generated from images of the ROI 102 captured using an image capture device of a video-based patient monitoring system configured in accordance with various embodiments of the present technology. The visual indicators illustrated in the images 1521-1524 can correspond to changes in depth computed by the system (e.g., to the signs and/or magnitudes of computed changes in depth) and/or to a current position within a cycle of the patient's breathing relative to one or more threshold target tidal volumes (e.g., the threshold target tidal volumes 1495-1498 illustrated in FIG. 14).

Figures 15A, 15B, 15C, 15D:
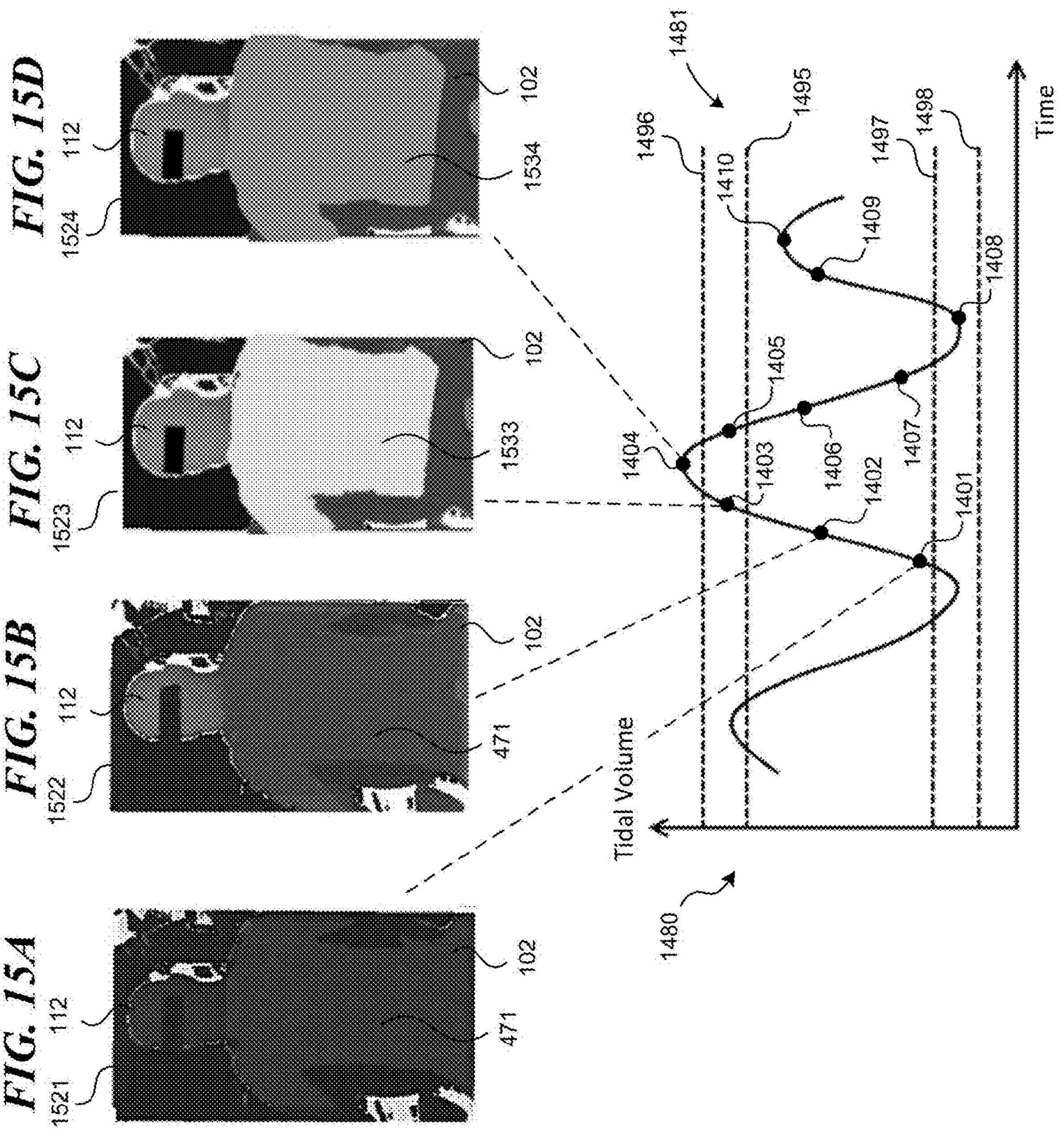
FIGS. 15A-15D are schematic views of images of a region of interest generated from images captured using an image capture device of a video-based patient monitoring system configured in accordance with various embodiments of the present technology.

In some embodiments, the system can display a visualization of the patient's breathing in real-time such that the current display corresponds to a current position of the patient's breathing within the patient's breathing cycle relative to one or more of the threshold target tidal volumes 1495-1498. For example, the system can display the generated image 1521 (FIG. 15A) at point 1401 along the tidal volume signal 1481 (FIG. 14) and/or can display the generated image 1522 (FIG. 15B) at point 1402 along the tidal volume signal 1481. As discussed above, a user viewing the sequence of images 1521 and 1522 can quickly and easily determine that the patient 112 is breathing, is currently inhaling, and is nearing the end of the inhalation portion of the patient's breathing cycle. In these and other embodiments, as the tidal volume signal 1481 meets and/or exceeds the threshold target tidal volume 1495, the system can change the visual indicator(s) displayed within the ROI 102 and/or can trigger an audio and/or visual alert. For example, the system can display the generated image 1523 (FIG. 15C) at point 1403 along the tidal volume signal 1481. As shown in FIG. 15C, the system has replaced the first color 471 in the ROI 102 with a third color 1533 in the image 1523. In some embodiments, the third color 1533 can indicate that the tidal volume signal 1481 has met and/or exceeded the threshold target tidal volume 1495. Thus, a user viewing the sequence of images 1521, 1522, and 1523 can quickly and easily see that the patient 112 is breathing, is currently inhaling, and has inhaled enough air to meet and/or exceed the threshold target tidal volume 1495.

Although the third color 1533 is illustrated in the image 1523 as spatially uniform across all regions in the ROI 102, the third color 1533 in other embodiments can spatially vary across the regions in the ROI 102. For example, various shades of the third color 1533 can be used to provide an indication of the amount of excursion a particular region of the ROI 102 experienced across two or more images in a video sequence. In these and other embodiments, the intensity and/or shade of the third color 1533 can vary (e.g., increase and/or decrease) across two or more generated images as the tidal volume increases and/or decreases to, for example, provide an indication of the current position of the patient's breathing within the patient's breathing cycle. In these and still other embodiments, the system can trigger other audio and/or visual alerts in addition to or in lieu of the third color 1533. For example, the system (i) can display a check mark or other graphic and/or (ii) can trigger a first audio alert/alarm to indicate that the patient's breathing has met and/or exceeded the threshold target tidal volume 1495.

As discussed above, in some embodiments a user and/or the system can set and/or define a second threshold target tidal volume 1496 (FIG. 14) in addition to or in lieu of the threshold target tidal volume 1495. For example, a user and/or the system can define and/or set the threshold target tidal volume 1496 such that it represents a volume of air above which the patient 112 is at risk of hyperventilation. In these and other embodiments, the threshold target tidal volumes 1495 and 1496 can define a range of tidal volumes indicative of normal ventilation for a particular patient 112. As the tidal volume signal 1481 (FIG. 14) meets and/or exceeds the threshold target tidal volume 1496, the system can change the visual indicator(s) displayed within the ROI 102 and/or can trigger an audio and/or visual alert/alarm to alert a user that the patient 112 is at risk of hyperventilation and/or that the patient's breathing is abnormal (e.g., outside of the range defined by the threshold target tidal volumes 1495 and 1496). For example, the system can display the generated image 1524 (FIG. 15D) at point 1404 along the tidal volume signal 1481. As shown in FIG. 15D, the system has replaced the third color 1533 in the ROI 102 with a fourth color 1534 in the image 1524. In some embodiments, the fourth color 1534 can indicate that the tidal volume signal 1481 has met and/or exceeded the threshold target tidal volume 1496. Thus, a user viewing the sequence of images 1521, 1522, 1523, and/or 1524 can quickly and easily see that the patient 112 is breathing, is currently inhaling, and has inhaled enough air to meet and/or exceed the threshold target tidal volume 1496. Although the fourth color 1534 is illustrated in the image 1522 as spatially uniform across all regions in the ROI 102, the fourth color 1534 in other embodiments can spatially vary across the regions in the ROI 102. For example, various shades of the fourth color 1534 can be used to provide an indication of the amount of excursion a particular region of the ROI 102 experienced across two or more images in a video sequence. In these and other embodiments, the intensity and/or shade of the fourth color 1534 can vary (e.g., increase and/or decrease) across two or more generated images as the tidal volume increases and/or decreases to, for example, provide an indication of the current position of the patient's breathing within the patient's breathing cycle. In these and still other embodiments, the system can trigger other audio and/or visual alerts/alarms in addition to or in lieu of the fourth color 1534. For example, the system (i) can display an "X" or other graphic, (ii) can flash the display, and/or (iii) can trigger a second audio alert/alarm to indicate that the patient's breathing has met and/or exceeded the threshold target tidal volume 1496.

In some embodiments, as the tidal volume signal 1481 (FIG. 14) returns below the second threshold target tidal volume 1496, the system can display the third color 1533 within the ROI 102 (similar to the generated image 1521 shown in FIG. 15A) until the tidal volume signal 1481 meets and/or drops below the threshold target tidal volume 1495. In these and other embodiments, the system can display the second color 472 within the ROI 102 as the tidal volume signal 1481 meets and/or drops below the threshold target tidal volume 1496 and/or 1495 to indicate that the patient 112 is currently exhaling. For example, the system can display the image 1641 (FIG. 16A) at point 1405 along the tidal volume signal 1481 (FIG. 14); display the generated image 1642 (FIG. 16B) at point 1406 along the tidal volume signal 1481; and/or display the generated image 1643 (FIG. 16C) at point 1407 along the tidal volume signal 1481. As discussed above, a user viewing the sequence of images 1641, 1642, and/or 1643 can quickly and easily determine that the patient 112 is breathing, is currently exhaling, and is nearing the end of the exhalation portion of the patient's breathing cycle.

Figures 16A, 16B, 16C, 16D:
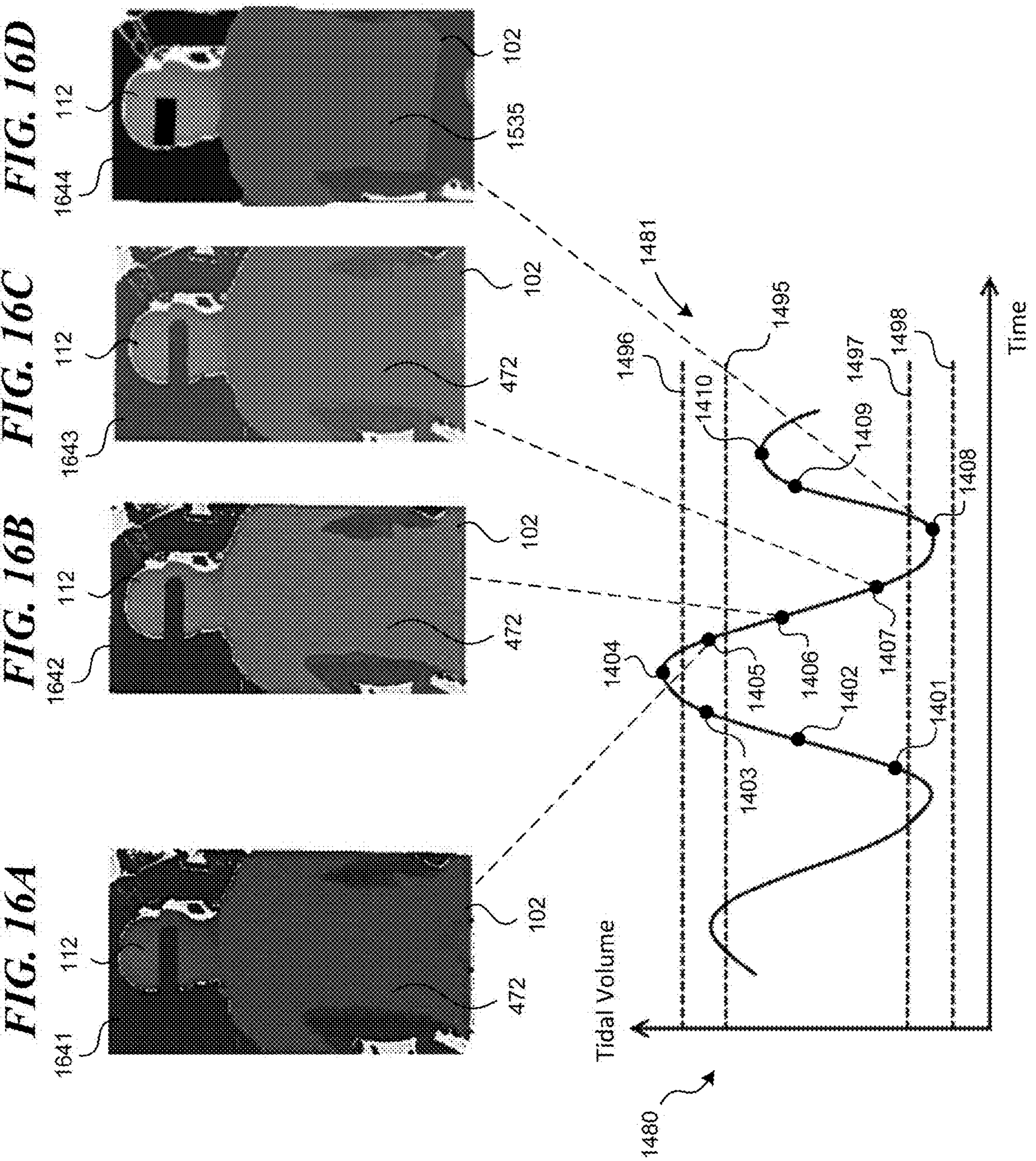
FIGS. 16A-16D are schematic views of images of a region of interest generated from images captured using an image capture device of a video-based patient monitoring system configured in accordance with various embodiments of the present technology.

As discussed above, in some embodiments a user and/or the system can set and/or define a threshold target tidal volume 1497. For example, a user and/or the system can define and/or set the threshold target tidal volume 1497 such that it represents a volume of air exhaled that, if not met, can indicate the patient 112 is experiencing one or more medical conditions, such as obstructive lung disease. In these and other embodiments, as the tidal volume signal 1481 (FIG. 14) meets and/or drops below the threshold target tidal volume 1497, the system can change the visual indicator(s) displayed within the ROI 102 and/or can trigger an audio and/or visual alert/alarm. For example, the system can display the generated image 1644 (FIG. 16D) at point 1408 along the tidal volume signal 1481. As shown in FIG. 16D, the system has replaced the second color 472 in the ROI 102 with a fifth color 1535 in the image 1644. In some embodiments, the fifth color 1535 can indicate that the tidal volume signal 1481 has met and/or dropped below the threshold target tidal volume 1497. Thus, a user viewing the sequence of images 1641, 1642, 1643, and/or 1644 can quickly and easily see that the patient 112 is breathing, is currently exhaling, and has exhaled enough air to meet and/or drop below the threshold target tidal volume 1497.

Although the fifth color 1535 is illustrated in the image 1644 as spatially uniform across all regions in the ROI 102, the fifth color 1535 in other embodiments can spatially vary across the regions in the ROI 102. For example, various shades of the fifth color 1535 can be used to provide an indication of the amount of excursion a particular region of the ROI 102 experienced across two or more images in a video sequence. In these and other embodiments, the intensity and/or shade of the fifth color 1535 can vary (e.g., increase and/or decrease) across two or more generated images as the tidal volume increases and/or decreases to, for example, provide an indication of the current position of the patient's breathing within the patient's breathing cycle. In these and still other embodiments, the system can trigger other audio and/or visual alerts/alarms in addition to or in lieu of the fifth color 1535. For example, the system (i) can display a check mark or other graphic and/or (ii) can trigger a third audio alert/alarm to indicate that the patient's breathing has met and/or dropped below the threshold target tidal volume 1497.

As discussed above, the threshold target tidal volume 1497 can represent a target volume of air exhaled from a patient's lungs. For example, a user and/or the system can define and/or set the threshold target tidal volume 1497 to represent a target volume of air that, if not met, can indicate the patient 112 is experiencing various medical conditions, such as obstructive lung disease. Thus, if a patient 112 is unable to or has difficulty exhaling enough air out of his/her lungs such that the tidal volume signal 1481 does not meet and/or drop below the threshold target tidal volume 1497 in one or more cycles of the patient's breathing (e.g., a scenario not illustrated by the tidal volume signal 1481 in FIG. 14), the system can trigger one or more audio and/or visual alerts/alarms to notify a user of the system. For example, the system (i) can display an "X" or other graphic, (ii) can flash the display, and/or (iii) can trigger a fourth audio alert/alarm to indicate that the patient's breathing did not meet and/or drop below the threshold target tidal volume 1497.

As discussed above, in some embodiments a user and/or the system can set and/or define a threshold target tidal volume 1498 (FIG. 14) in addition to or in lieu of the threshold target tidal volume 1497. For example, a user and/or the system can define and/or set the threshold target tidal volume 1498 such that it represents a volume of air below which the system can determine that patient 112 is not breathing and/or the patient's breathing is strained, inhibited, restricted, and/or obstructed. In these and other embodiments, the threshold target tidal volumes 1497 and 1498 can define a range of tidal volumes indicative of normal ventilation for a particular patient 112. As the tidal volume signal 1481 (FIG. 14) meets and/or drops below the threshold target tidal volume 1498 (e.g., a scenario not illustrated by the tidal volume signal 1481 in FIG. 14), the system can change the visual indicator(s) displayed within the ROI 102 and/or can trigger an audio and/or visual alert/alarm to alert a user that the patient 112 is not breathing; that the patient's breathing is strained, inhibited, restricted, and/or obstructed; and/or that the patient's breathing is abnormal (e.g., outside of the range defined by the threshold target tidal volumes 1497 and 1498). For example, the system can display a sixth color (not shown) within the ROI of a generated image (not shown) as the tidal volume signal 1481 meets and/or drops below the threshold target tidal volume 1498. In some embodiments, the sixth color can indicate that the tidal volume signal 1481 has met and/or dropped below the threshold target tidal volume 1498. Thus, a user viewing the sequence of images 1641, 1642, 1643, 1644, and/or the generated image (not shown) showing the sixth color can quickly and easily see that the patient 112 is breathing, is currently exhaling, and is exhaling an amount of air beyond the threshold target tidal volume 1498. In some embodiments, the sixth color can be spatially uniform across all regions in the ROI 102, or the sixth color can spatially vary (e.g., with various shades of the sixth color) across the regions in the ROI 102 (e.g., to provide an indication of the amount of excursion a particular region of the ROI 102 experienced across two or more images in a video sequence). In these and other embodiments, the intensity and/or shade of the sixth color can vary (e.g., increase and/or decrease) across two or more generated images as the tidal volume increases and/or decreases to, for example, provide an indication of the current position of the patient's breathing within the patient's breathing cycle. In these and still other embodiments, the system can trigger other audio and/or visual alerts/alarms in addition to or in lieu of the sixth color. For example, the system (i) can display an "X" or other graphic, (ii) can flash the display, and/or (iii) can trigger a fifth audio alert/alarm to indicate that the patient's breathing has met and/or exceeded the threshold target tidal volume 1496.

As shown in FIG. 14, the points 1408-1410 along the tidal volume signal 1481 are positioned on a subsequent cycle of the patient's breathing. In some embodiments, the system can display a visualization of the patient's breathing using generated images (not shown) similar to the images 1521 and 1522 (FIGS. 15A and 15B) at points 1408 and/or 1409 to indicate that the patient 112 is breathing, to indicate that the patient 112 is currently inhaling, and to indicate an amount (e.g., a volume) of air within the patient's lungs.

In contrast with the previous cycle of the patient's breathing, during the subsequent cycle of the patient's breathing, the patient 112 begins exhaling before the tidal volume signal 1481 meets and/or exceeds the threshold target tidal volume 1495. As discussed above, the threshold target tidal volume 1495 in some embodiments can represent a volume of air below which the patient 112 is at risk of hypoventilation. The system can notify the user that the patient's breathing did not meet and/or exceed the threshold target tidal volume 1495 (e.g., that the patient 112 did not inhale enough air and/or is at risk of hypoventilation) by changing (e.g., the color of) the visual indicators within the ROI 102 of the visualization of the patient's breathing cycle, displaying one or more other graphics, and/or triggering one or more other audio and/or visual alerts/alarms. For example, the system (i) can display a seventh color (not shown) within the ROI 102, (ii) can display an "X" or other graphic, (iii) can flash the display, and/or (iv) can trigger a sixth audio alert and/or alarm.

FIGS. 17A-17D are schematic views of images 1761-1764, respectively, of an aggregate ROI 102 generated from images captured using an image capture device of a video-based patient monitoring system. The images 1761-1764 can be generated from images of the ROI 102 captured using an image capture device of a video-based patient monitoring system configured in accordance with various embodiments of the present technology and in a manner similar to the images 1261-1263 (FIGS. 12A-12C). Also similar to the visual indicators illustrated in the images 1261-1263, the visual indicators illustrated in the images 1761-1764 can correspond to changes in depth computed by the system (e.g., to the signs and/or magnitudes of computed changes in depth).

In some embodiments, the amount of the ROI 102 filled with one or more visual indicators in the images 1761-1764 can correspond to a position along the patient's breathing cycle and/or to an amount (e.g., a volume) of air within the patient's lungs. For example, the system can display the image 1761 (FIG. 17A) at point 1401 along the tidal volume signal 1481 (FIG. 14), and the system can display the image 1762 (FIG. 17B) at point 1402 along the tidal volume signal 1481. The amount of the ROI 102 filled with the first color 471 in the image 1762 is greater than the amount of the ROI 102 filled with the first color 471 in the image 1761. As a result, a user viewing the sequence of images 1761 and 1762 can quickly and easily determine that the patient 112 is breathing (indicated by the presence of a visual indicator) and is currently inhaling (indicated by the presence of the first color 471). Furthermore, based on the amount of the ROI 102 filled by the first color 471, the system can provide the user an indication of the current position of the patient's breathing within the patient's breathing cycle and/or an indication of the amount (e.g., volume) of air within the patient's lungs.

Figures 17A, 17B, 17C, 17D:
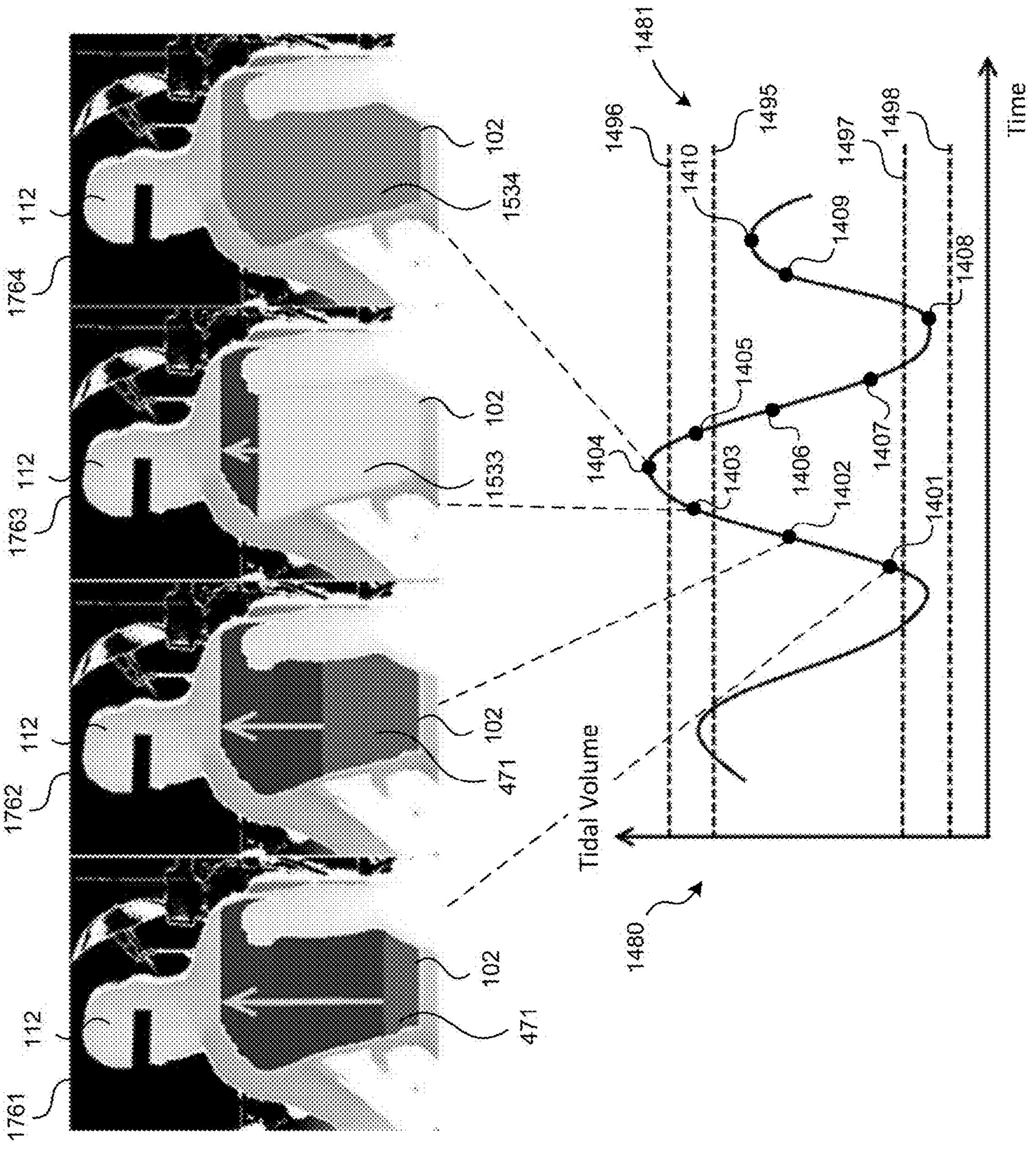
FIGS. 17A-17D are schematic views of images of a region of interest generated from images captured using an image capture device of a video-based patient monitoring system configured in accordance with various embodiments of the present technology.

In some embodiments, as the tidal volume signal 1481 (FIG. 14) meets and/or exceeds the threshold target tidal volume 1495, the system can change the visual indicators displayed within the ROI 102, can display one or more other graphics, and/or can trigger one or more other audio and/or visual alerts/alarms. For example, the system can display the image 1763 (FIG. 17C) at point 1403 along the tidal volume signal 1481. As shown in FIG. 17C, the system has replaced the first color 471 in the ROI 102 with the third color 1533 in the image 1763. In addition, the amount of the ROI 102 filled with the third color 1533 in the image 1763 is greater than the amount of the ROI 102 filled with the first color 471 in the images 1761 and 1762 (FIGS. 17A and 17B). As a result, a user viewing the sequence of images 1761, 1762, and/or 1763 can quickly and easily determine that the patient 112 is breathing (indicated by the presence of a visual indicator), that the patient 112 is currently inhaling (indicated by the sequence of the first color 471 to the third color 1533), and that the amount of air within the patient's lungs meets and/or exceeds the threshold target tidal volume 1495 (indicated by the presence of the third color 1533 and/or by the amount of the ROI 102 filled within the image 1763).

In these and other embodiments, as the tidal volume signal 1481 (FIG. 14) meets and/or exceeds the threshold target tidal volume 1496, the system can change the visual indicators displayed within the ROI 102, can display one or more other graphics, and/or can trigger one or more other audio and/or visual alerts/alarms. For example, the system can display the image 1764 (FIG. 17D) at point 1404 along the tidal volume signal 1481 (above the second threshold 1496). As shown in FIG. 17D, the system can display the fourth color 1534 within the ROI 102. In addition, the amount of the ROI 102 filled with the fourth color 1534 is greater than the amount of the ROI 102 filled with the first color 471 in the images 1761 and 1762 (FIGS. 17A and 17B) as well as the amount of the ROI 102 filled with the third color 1533 in the image 1763. As a result, a user viewing the sequence of images 1761, 1762, 1763, and/or 1764 can quickly and easily determine that that the patient 112 is breathing (indicated by the presence of a visual indicator), that the patient 112 is currently inhaling (indicated by the sequence of the first color 471 to the third color 1533 and/or to the fourth color 1534), and that the amount of air within the patient's lungs meets and/or exceeds the threshold target tidal volumes 1495 and/or 1496 (indicated by the presence of the third color 1533 and/or the fourth color 1534 and/or by the amount of the ROI 102 filled within the image 1764). In embodiments where the threshold target tidal volume 1496 helps define a range of normal patient ventilation and/or represents an amount of air above which the patient 112 is at risk of hyperventilation, the system can notify the user that the patient's breathing is outside of the range of normal patient ventilation and/or that the patient 112 is at risk of hyperventilation by displaying the fourth color 1534 within the ROI 102. In these and still other embodiments, the system can flash the display and/or trigger other audio and/or visual alerts/alarms to alert the user that the patient's breathing has exceeded the threshold target tidal volume 1496.

FIGS. 18A-18D are schematic views of images 1871-1874, respectively, of an aggregate ROI 102 generated from images captured using an image capture device of a video-based patient monitoring system. The images 1871-1874 can be generated from images of the ROI 102 captured using an image capture device of a video-based patient monitoring system configured in accordance with various embodiments of the present technology and in a manner similar to the images 1371-1373 (FIGS. 13A-13C). Also similar to the visual indicators illustrated in the images 1371-1373, the visual indicators illustrated in the images 1871-1874 can correspond to changes in depth computed by the system (e.g., to the signs and/or magnitudes of computed changes in depth). The amount of the ROI 102 filled with one or more visual indicators in the images 1871-1874 can correspond to a position along the patient's breathing cycle and/or to an amount (e.g., a volume) of air within the patient's lungs.

In some embodiments, as the tidal volume signal 1481 (FIG. 14) returns below the second threshold target tidal volume 1496, the system can display the third color 1533 within the ROI 102 (similar to the generated image 1763 shown in FIG. 17C) until the tidal volume signal 1481 meets and/or drops below the threshold target tidal volume 1495 (e.g., to indicate that the amount of air within the patient's lungs is currently at or above the threshold target tidal volume 1495 but within the range of normal ventilation for the patient 112 defined by the threshold target tidal volumes 1495 and 1496). In these and other embodiments, the system can display the image 1871 (FIG. 18A) at point 1405 along the tidal volume signal 1481. In these and other embodiments, the system can display the image 1872 (FIG. 18B) at point 1406 along the tidal volume signal 1481 and/or display the image 1873 (FIG. 18C) at point 1407 along the tidal volume signal 1481. The amount of the ROI 102 filled with the second color 472 in the image 1871 is greater than the amount of the ROI 102 filled with the second color 472 in the images 1872 and 1873. Similarly, the amount of the ROI 102 filled with the second color 472 in the image 1872 is greater than the amount of the ROI 102 filled with the second color 472 in the image 1873. As a result, a user viewing a sequence of images 1871, 1872, and/or 1873 can quickly and easily determine that the patient 112 is breathing (indicated by the presence of a visual indicator) and is currently exhaling (indicated by the presence of the second color 472). Furthermore, based on the amount of the ROI 102 filled by the visual indicator(s), the system can provide the user an indication of the current position of the patient's breathing within the patient's breathing cycle and/or an indication of the amount (e.g., volume) of air within the patient's lungs.

Figures 18A, 18B, 18C, 18D:
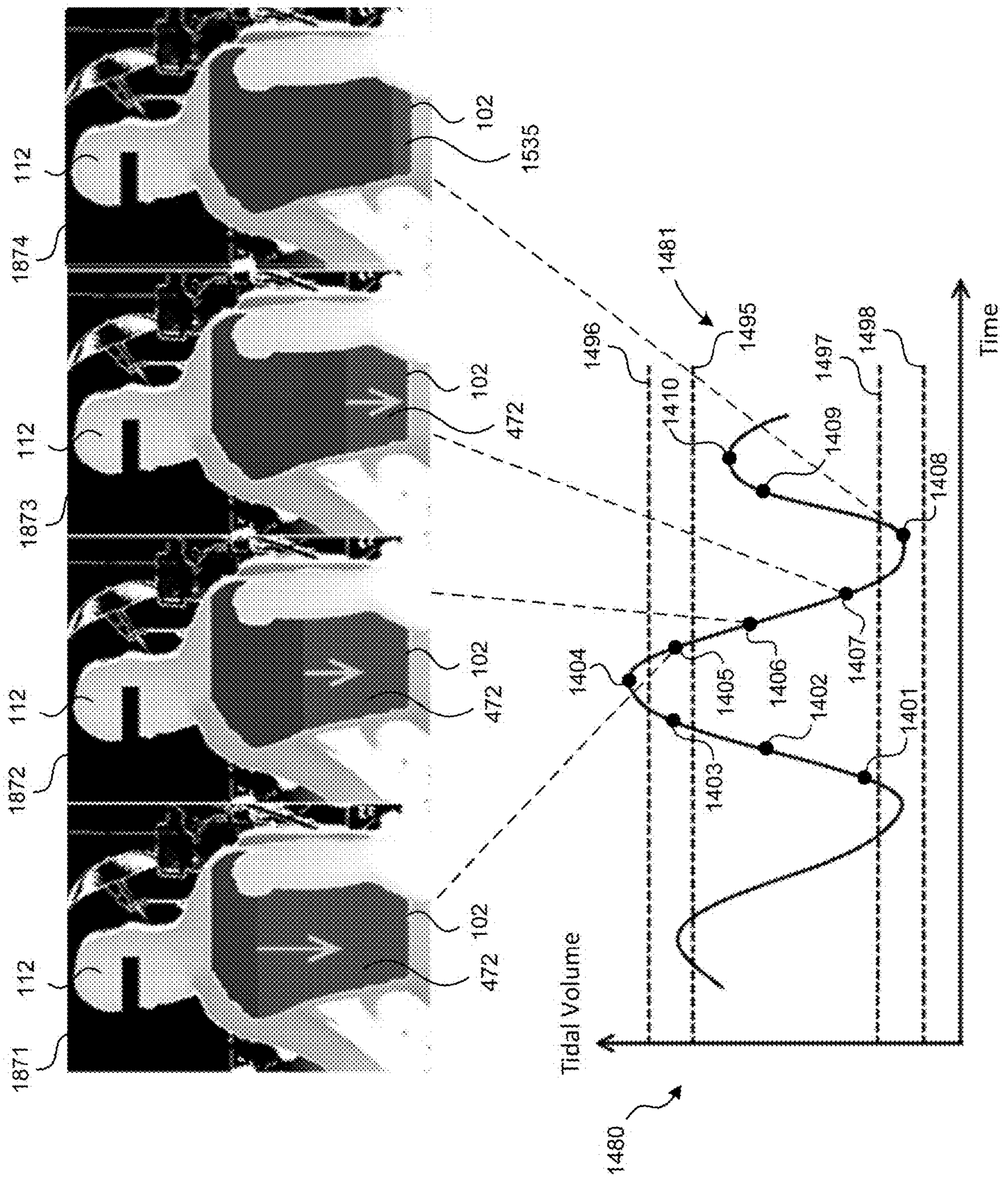
FIGS. 18A-18D are schematic views of images of a region of interest generated from images captured using an image capture device of a video-based patient monitoring system configured in accordance with various embodiments of the present technology.

In some embodiments, as the tidal volume signal 1481 (FIG. 14) meets and/or drops below the threshold target tidal volume 1497, the system can change the visual indicators displayed within the ROI 102, can display one or more other graphics, and/or can trigger one or more other audio and/or visual alerts/alarms. For example, the system can display the image 1874 (FIG. 18D) at point 1408 along the tidal volume signal 1481. As shown in FIG. 18D, the system has replaced the second color 472 in the ROI 102 with the fifth color 1535 in the image 1874. In addition, the amount of the ROI 102 filled with the fifth color 1535 in the image 1874 is less than the amount of the ROI 102 filled with the second color 472 in the images 1871, 1872, and 1873 (FIGS. 18A-18C). As a result, a user viewing the sequence of images 1871, 1872, 1873, and/or 1874 can quickly and easily determine that that the patient 112 is breathing (indicated by the presence of a visual indicator), that the patient 112 is currently exhaling (indicated by the sequence of the second color 472 to the fifth color 1535), and that the amount of air within the patient's lungs meets and/or is below the threshold target tidal volume 1497 (indicated by the presence of the fifth color 1535 and/or by the amount of the ROI 102 filled within the image 1874).

In these and other embodiments, as the tidal volume signal 1481 (FIG. 14) meets and/or drops below the threshold target tidal volume 1498, the system can change the visual indicators displayed within the ROI 102, can display one or more other graphics, and/or can trigger one or more other audio and/or visual alerts/alarms. For example, when the tidal volume signal 1481 meets and/or drops below the threshold target tidal volume 1498 (e.g., a scenario not illustrated by the tidal volume signal 1481 in FIG. 14), the system can display a generated image (not shown) where less of the ROI 102 is filled with a visual indicator (e.g., the sixth color) than is filled in the image 1874 (FIG. 18D). As a result, a user can quickly and easily determine that that the patient 112 is breathing (indicated by the presence of a visual indicator), that the patient 112 is currently exhaling (indicated by the sequence of the second color 472 to the fifth color 1535 and/or to the sixth color), and that the amount of air within the patient's lungs meets and/or is below the threshold target tidal volumes 1497 and 1498 (indicated by the presence of the fifth color 1535 and/or the sixth color and/or by the amount of the ROI 102 filled within the generated image). In embodiments where the threshold target tidal volume 1498 helps define a range of normal patient ventilation, the system can notify the user that the patient's breathing is outside of the range of normal patient ventilation. In these and still other embodiments, the system can flash the display and/or trigger other audio and/or visual alerts/alarms to alert the user that the patient's breathing has dropped below the threshold target tidal volume 1498.

Figures 19A, 19B, 19C:
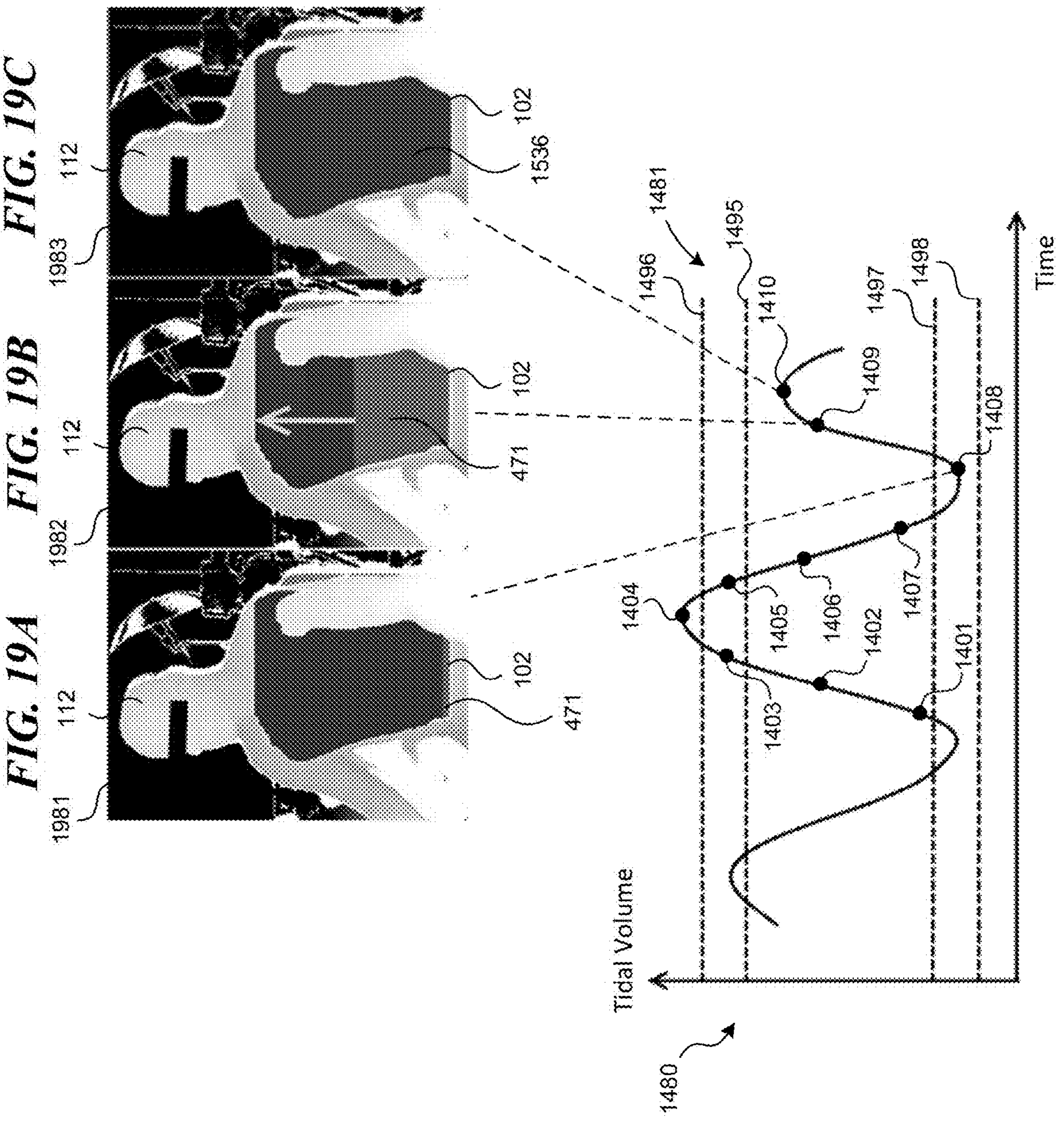
FIGS. 19A-19C are schematic views of images of a region of interest generated from images captured using an image capture device of a video-based patient monitoring system configured in accordance with various embodiments of the present technology.

FIGS. 19A-19C are schematic views of images 19881-1983, respectively, of an aggregate ROI 102 generated from images captured using an image capture device of a video-based patient monitoring system. The images 1981-1983 can be generated from images of the ROI 102 captured using an image capture device of a video-based patient monitoring system configured in accordance with various embodiments of the present technology and in a manner similar to the images 1261-1263 and/or 1761-1764 (FIGS. 12A-12C and 17A-17D, respectively). Also similar to the visual indicators illustrated in the images 1261-1263 and/or 1761-1764, the visual indicators illustrated in the images 1981-1983 can correspond to changes in depth computed by the system (e.g., to the signs and/or magnitudes of computed changes in depth). The amount of the ROI 102 filled with one or more visual indicators in the images 1981-1983 can correspond to a position along the patient's breathing cycle and/or to an amount (e.g., a volume) of air within the patient's lungs.

In some embodiments, as the tidal volume signal 1481 (FIG. 14) is at or below the threshold target tidal volume 1497, the system can display a generated image (not shown) filled with the fifth color 1535 (similar to 1874 in FIG. 18D) until the tidal volume signal meets and/or exceeds the threshold target tidal volume 1497 (e.g., to indicate that the amount of air within the patient's lungs is currently at or below the threshold target tidal volume 1497 but within the range of normal ventilation for the patient 112 defined by the threshold target tidal volumes 1497 and 1498). In these and other embodiments, the system can display the image 1981 (FIG. 19A) at point 1408 along the tidal volume signal 1481. In these and other embodiments, the system can display the image 1982 (FIG. 19B) at point 1409 along the tidal volume signal 1481. The amount of the ROI 102 filled with the first color 471 in the image 1982 is greater than the amount of the ROI 102 filled with the first color 471 in the image 1981. As a result, a user viewing a sequence of images 1981 and 1982 can quickly and easily determine that the patient 112 is breathing (indicated by the presence of a visual indicator) and is currently inhaling (indicated by the presence of the first color 471). Furthermore, based on the amount of the ROI 102 filled by the first color 471, the system can provide the user an indication of the current position of the patient's breathing within the patient's breathing cycle and/or an indication of the amount (e.g., volume) of air within the patient's lungs.

As discussed above, in contrast with the previous cycle of the patient's breathing, the tidal volume signal 1481 plateaus and begins to decrease in the subsequent cycle (as shown by the tidal volume signal 1481 at points 1408-1410 illustrated in FIG. 14) before the tidal volume signal 1481 meets and/or exceeds the threshold target tidal volume 1495 of the patient's breathing (e.g., the patient 112 starts to exhale before the tidal volume signal 1481 reaches the threshold target tidal volume 1495). As discussed above, the threshold target tidal volume 1495 in some embodiments can represent a volume of air below which the patient 112 is at risk of hypoventilation. The system can notify the user that the patient's breathing did not meet and/or exceed the threshold target tidal volume 1495 (e.g., that the patient 112 did not inhale enough air and/or is at risk of hypoventilation) by changing (e.g., the color of) the visual indicators within the ROI 102 of the visualization of the patient's breathing cycle, displaying one or more other graphics, and/or triggering one or more other audio and/or visual alerts/alarms. For example, at point 1410 along the tidal volume signal 1481, the system can transition from displaying an ROI 102 filled with a visual indicator of the first color 471 to displaying an ROI 102 filled with a visual indicator of the second color 472 (to depict exhalation) without displaying the ROI 102 filled with the third color 1533. In these and other embodiments, the system can (e.g., temporarily) display the image 1983 (FIG. 19C) at point 1410 along the tidal volume signal 1481 as the patient 112 begins to exhale. As shown in the image 1983, a greater amount of the ROI 102 is filled with a visual indicator than the amount of the ROI 102 filled with a visual indicator in the images 1981 and 1982 (FIGS. 19A and 19B). A sixth color 1536, however, is used as a visual indicator in the image 1983. As a result a user viewing the sequence of images 1981, 1982, and/or 1983 can quickly and easily determine that the patient 112 is breathing (indicated by the presence of a visual indicator within the ROI 102) and that the patient 112 has finished inhaling and has started exhaling (indicated by the transition of visual indicators from the first color 471 to the second color 472 and/or to the sixth color 1536 within the ROI 102). In addition, the user can also determine that the patient 112 did not inhale enough air to meet and/or exceed the threshold target tidal volume 1495 (indicated by the presence of the sixth color 1536, by the transition of the first color 471 to the second color 472 and/or the sixth color 1536 without first displaying the third color 1533, and/or by the fact that the sixth color 1536 does not fill the ROI 102) and/or the patient 112 might be at risk of hypoventilation. In these and other embodiments, the system (i) can display an "X" or other graphic, (ii) can flash the display, and/or (iii) can trigger a sixth audio alert/alarm to alert the user that the patient's breathing did not reach the threshold target tidal volume 1495. In these and still other embodiments, the system can similarly change (e.g., the color of) the visual indicators displayed within the ROI 102, display one or more other graphics (e.g., an "X"), and/or trigger one or more other audio and/or visual alerts/alarms to notify a user when the patient 112 does not exhale enough air for the tidal volume signal 1481 to meet and/or drop below the threshold target tidal volume 1497 (e.g., defined and/or set to represent a volume of air that, if not met, can indicate the patient 112 is suffering one or more medical conditions, such as obstructive lung disease).

Figure 20:
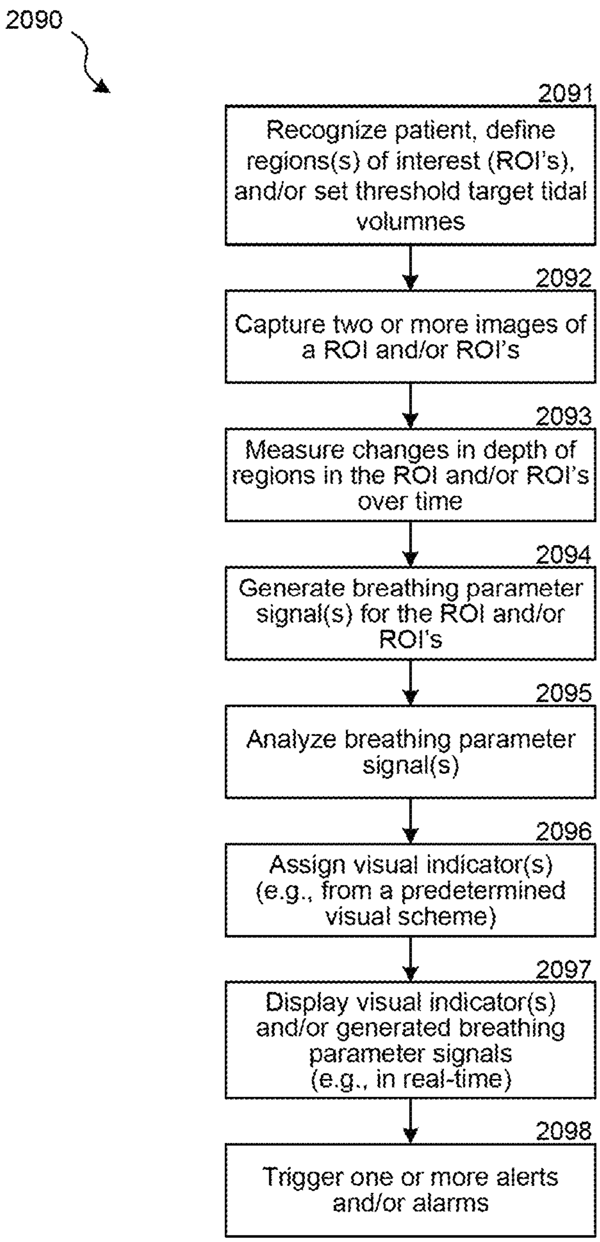
FIG. 20 is a flow diagram illustrating a video-based patient monitoring routine of a method for detecting and monitoring breathing in a patient in accordance with various embodiments of the present technology.

FIG. 20 is a flow diagram illustrating a video-based patient monitoring routine 2090 of a method for detecting and monitoring breathing in a patient in accordance with various embodiments of the present technology. All or a subset of the steps of the routine 2090 can be executed by various components of a video-based patient monitoring system and/or a user of the system (e.g., a caregiver, a clinician, a patient, etc.). For example, all or a subset of the steps of the routine 2090 can be executed by (i) components of the video-based patient monitoring system 100 shown in FIG. 1 and/or (ii) components of the video-based patient monitoring system 200 shown in FIG. 2.

The routine 2090 can begin at block 2091 by recognizing a patient within a field of view (FOV) of the image capture device, defining one or more regions of interest (ROI's) on the patient, and/or setting one or more threshold target tidal volumes. In some embodiments, the routine 2090 can recognize the patient by identifying the patient using facial recognition hardware and/or software of the image capture device. In these embodiments, the routine 2090 can display the name of the patient on a display screen once the routine 2090 has identified the patient. In these and other embodiments, the routine 2090 can recognize a patient within the FOV of the image capture device by determining a skeleton outline of the patient and/or by recognizing one or more characteristic features (e.g., a torso of a patient). In these and still other embodiments, the routine 2090 can define one or more ROI's on the patient in accordance with the discussion above with respect to FIGS. 1 and/or 3. For example, the routine 2090 can define one or more ROI's on the patient using extrapolation from a point on the patient, using inferred positioning from proportional and/or spatial relationships with the patient's face, using parts of the patient having similar depths from the camera 114 as a point, using one or more features on the patient's clothing, using user input, etc.

In some embodiments, the routine 2090 can define the one or more threshold target tidal volumes based, at least in part, on one or more patient factors. For example, the routine 2090 can define the one or more threshold target tidal volumes based on demographics and/or disease state(s) of the patient. In these and other embodiments, the routine 2090 can define one or more threshold target tidal volumes based on one or more previous breathing cycles of the patient. For example, the routine 2090 can monitor one or more previous breathing cycles of the patient to define one or more ranges of tidal volumes indicative of normal patient ventilation. In some embodiments, the routine 2090 can define (i) one or more inhalation target tidal volumes and/or (ii) one or more exhalation target tidal volumes. For example, the routine 2090 (a) can define an inhalation threshold target tidal volume representative of a volume of inhaled air below which the patient is at risk of hypoventilation and/or (b) can define an inhalation threshold target tidal volume representative of a volume of inhaled air above which the patient is at risk of hyperventilation. Additionally or alternatively, the routine 2090 (a) can define an exhalation threshold target tidal volume representative of a volume of exhaled air that, if not met, can indicate that the patient is suffering one or more medical conditions, such as obstructive lung disease and/or (b) can define an exhalation threshold target tidal volume representative of a volume of air that, if exceeded, can indicate that the patient is not breathing and/or that the patient's breathing is strained, inhibited, restricted, and/or obstructed.

At block 2092, the routine 2090 can capture two or more images of one or more ROI's. In some embodiments, the routine 2090 can capture the two or more images of the one or more ROI's by capturing a video sequence of the one or more ROI's. In these and other embodiments, the routine 2090 can capture the two or more images of the one or more ROI's by capturing separate still images of the one or more ROI's. The routine 2090 can capture the two or more still images at a rate faster than a period of the patient's respiration cycle to ensure that the two or more still images occur within one period of the patient's respiration cycle.

At block 2093, the routine 2090 can measure changes in depth of one or more regions in one or more ROI's over time. In some embodiments, the routine 2090 can measure changes in depth of regions in the one or more ROI's by computing a difference between a depth of a region of a ROI in a first captured image of the ROI and a depth of the same region in a second captured image of the ROI.

At block 2094, the routine 2090 can generate one or more breathing parameter signals. In some embodiments, the routine 2090 generates a volume gain signal and/or a volume loss signal for one or more ROI's. In these and other embodiments, the routine 2090 generates a tidal volume signal for one or more ROI's. In these and still other embodiments, the routine 2090 generates one or more other breathing parameter signals for one or more ROI's. For example, the routine 2090 can generate an inhalation-to-exhalation ratio for one or more ROI's, a degree of consistency value indicating consistency in the volume of each breath for one or more ROI's, a trending and/or an absolute minute volume signal for one or more ROI's, a respiratory rate signal for one or more ROI's, a SpO2 signal for one or more ROI's, and/or an absolute tidal volume signal for one or more ROI's, among others.

At block 2095, the routine 2090 can analyze one or more of the breathing parameter signals generated at block 2094 to determine one or more positions of the patient's breathing within the patient's breathing cycle. For example, the routine 2090 can determine whether the patient is currently breathing and/or whether the patient is currently inhaling and/or exhaling. In these and other embodiments, the routine 2090 can determine the one or more positions of the patient's breathing relative to one or more defined threshold target tidal volumes. For example, if the routine 2090 determines that the patient is currently inhaling, the routine 2090 can determine whether the tidal volume signal is at or above an inhalation threshold target tidal volume previously defined by the routine 2090. If the routine 2090 determines that the patient is currently exhaling, the routine 2090 can determine whether the tidal volume signal is at or below one or more exhalation threshold target tidal volumes defined by the routine 2090. In these and other embodiments, the routine 2090 can determine whether the tidal volume signal is within and/or outside one or more ranges of normal patient ventilation defined by the routine 2090.

At block 2096, the routine 2090 can assign one or more visual indicators to one or more regions in the one or more ROI's. In some embodiments, the one or more visual indicators can be colors, patterns, shades, concentrations, intensities, etc. In these and other embodiments, the routine 2090 can assign the one or more visual indicators in accordance with a predetermined visual scheme. In these and still other embodiments, the routine 2090 can assign one or more visual indicators to one or more regions in accordance with the discussion above with respect to FIGS. 4A-18C. For example, the routine 2090 can assign one or more visual indicators to the one or more regions based at least in part on the (e.g., sign and/or magnitude of a) measured/computed change in depth exhibited by a region over time (e.g., across two captured images of the one or more ROI), the position of the patient's breathing within the patient's breathing cycle, the patient's tidal volume signal relative to one or more threshold target tidal volumes, and/or the amount of air within the patient's lungs.

At block 2097, the routine 2090 can display one or more visual indicators assigned at block 2096 over corresponding regions of one or more ROI's and/or can display one or more of the breathing parameter signals generated at block 2094. In some embodiments, the routine 2090 can display the one or more visual indicators in accordance with the discussion above with respect to FIGS. 4A-18C. For example, the routine 2090 can display the one or more visual indicators (i) over a corresponding region in a corresponding ROI (e.g., over a corresponding portion of the patient), (ii) over all regions in the ROI, and/or (iii) over an amount of the ROI indicative of the position of the patient's breathing within the patient's breathing cycle and/or indication of the amount (e.g., volume) of air within the patient's lungs. In these and other embodiments, the routine 2090 can display a generated volume gain signal, a generated volume loss signal, a generated trending tidal volume signal, a generated absolute tidal volume signal, a generated trending minute volume signal, a generated absolute minute volume signal, a generated respiratory rate signal, a generated inhalation-to-exhalation ratio, a generated degree of consistency in the volume of each breath, and/or a generated SpO2 signal for one or more ROI's. In these and still other embodiments, the one or more visual indicators and/or one or more of the generated breathing parameter signals can be displayed in real-time. In these and other embodiments, the one or more visual indicators and/or one or more of the generated breathing parameter signals can be recorded such that they can be displayed at a later time (e.g., for a clinician to review). In these and still other embodiments, the one or more visual indicators and/or one or more of the breathing parameter signals can be displayed on a clinician's display, on a caregiver's display, and/or on a patient's display. For example, the one or more visual indicators and/or one or more of the breathing parameter signals can be displayed on a caregiver's display where the display is at a central station (e.g., in a hospital) and/or at a remote site from the patient.

At block 2098, the routine 2090 can trigger one or more alerts and/or alarms. In some embodiments, the routine 2090 can trigger the one or more alerts and/or alarms by changing the visual indicators displayed in the ROI 102, by flashing the display, by displaying one or more other graphics, and/or by triggering one or more other visual and/or audio alerts/alarms. For example, the routine 2090 can trigger the one or more alerts/alarms in accordance with the discussion above with respect to FIGS. 14-18C. In these and other embodiments, the routine 2090 can trigger the one or more alerts/alarms to indicate that the patient's tidal volume signal has met and/or exceeded an inhalation threshold target tidal volume and/or has fallen within a range of tidal volumes indicative of normal patient ventilation. In these and still other embodiments, the routine 2090 can trigger the one or more alerts/alarm to indicate that the patient's tidal volume signal has met and/or dropped below an exhalation threshold target tidal volume and/or has fallen within a range of tidal volumes indicative of normal patient ventilation. In these and yet other embodiments, the routine 2090 can trigger the one or more alerts/alarms when the patient is inhaling and (a) the patient's tidal volume signal does not meet or exceed an inhalation threshold target tidal volume below which the patient is at risk of hypoventilation and/or (b) the patient's tidal volume signal meets and/or exceeds an inhalation threshold target tidal volume above which the patient is at risk of hyperventilation. In these and other embodiments, the routine 2090 can trigger the one or more alerts/alarms when the patient is exhaling and (a) the patient's tidal volume signal does not meet and/or drop below an exhalation threshold target tidal volume indicating that the patient can be suffering one or more medical conditions, such as obstructive lung disease and/or (b) the patient's tidal volume signal meets and/or drops below an exhalation threshold target tidal volume indicating that the patient is not breathing and/or that the patient's breathing is strained, inhibited, restricted, and/or obstructed.

Although the steps of the routine 2090 are discussed and illustrated in a particular order, the routine 2090 in FIG. 20 is not so limited. In other embodiments, the routine 2090 can be performed in a different order. In these and other embodiments, any of the steps of the routine 2090 can be performed before, during, and/or after any of the other steps of the routine 2090. Moreover, a person of ordinary skill in the relevant art will readily recognize that the illustrated method can be altered and still remain within these and other embodiments of the present technology. For example, one or more steps of the routine 2090 illustrated in FIG. 20 can be omitted and/or repeated in some embodiments.

FIGS. 21-25 are schematic views of images 2101, 2211, 2321, 2431, and 2541, respectively, of an aggregate ROI 102 generated from images captured using an image capture device of a video-based patient monitoring system. The images 2101, 2211, 2321, 2431, and 2541 can be generated from images of the ROI 102 captured using an image capture device of a video-based patient monitoring system configured in accordance with various embodiments of the present technology and in a manner similar to the images discussed and/or illustrated in FIGS. 4A-19C above. The visual indicators illustrated in the images 2101, 2211, 2321, 2431, and 2541 can correspond to changes in depth computed by the system (e.g., to the signs and/or magnitudes of computed changes in depth).

Figure 23:
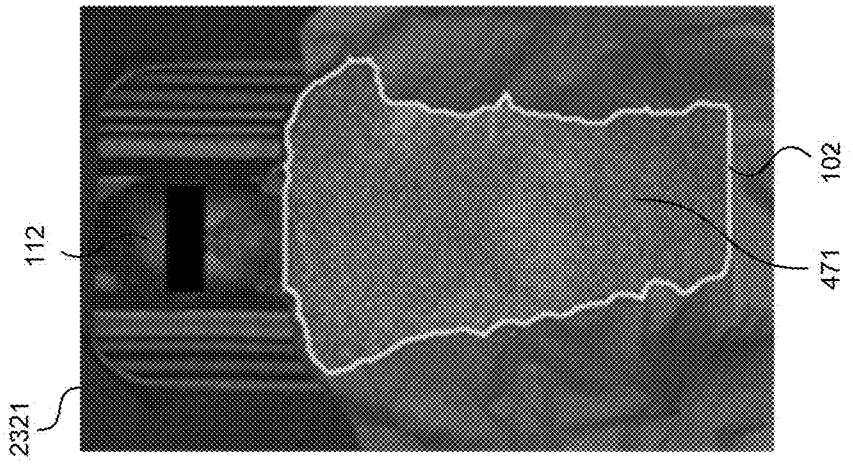
FIG. 23 is a schematic view of an infrared image of a region of interest generated from images captured using an image capture device of a video-based patient monitoring system configured in accordance with various embodiments of the present technology.
Figure 22:
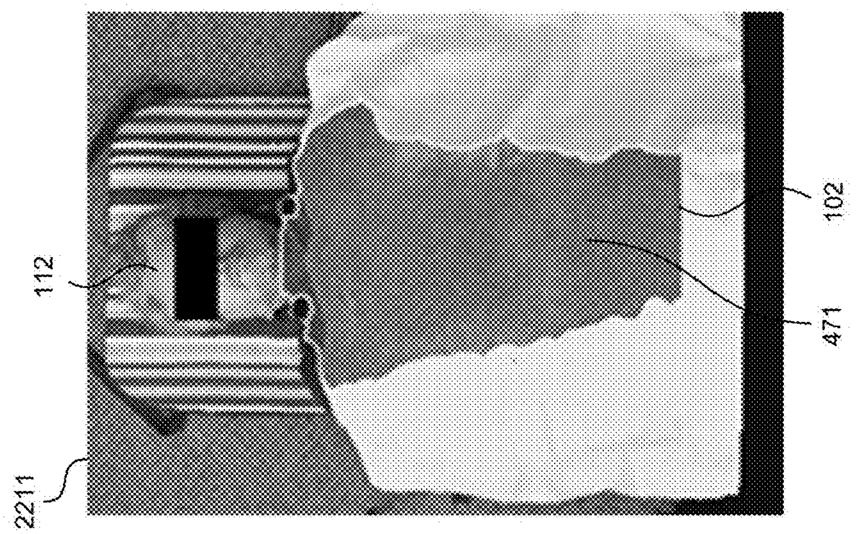
FIG. 22 is a schematic view of an RGB image of a region of interest generated from images captured using an image capture device of a video-based patient monitoring system configured in accordance with various embodiments of the present technology.
Figure 21:
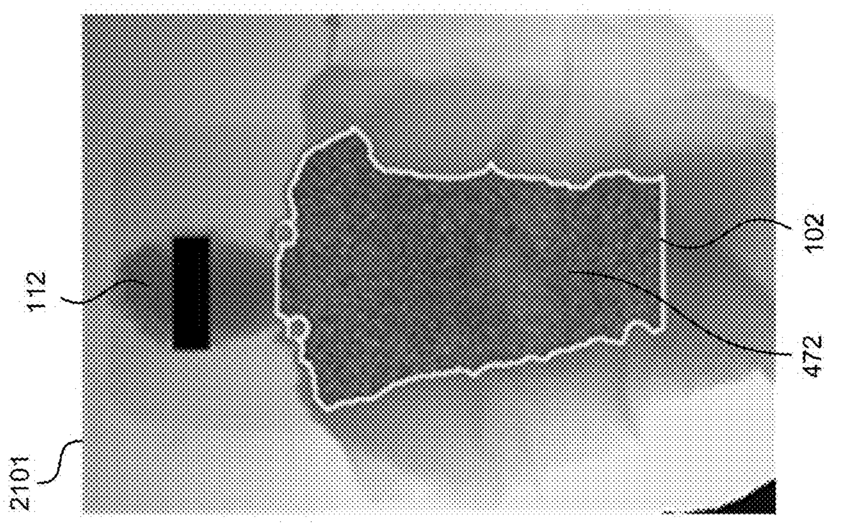
FIG. 21 is a schematic view of a depth image of a region of interest generated from images captured using an image capture device of a video-based patient monitoring system configured in accordance with various embodiments of the present technology.
Figure 24:
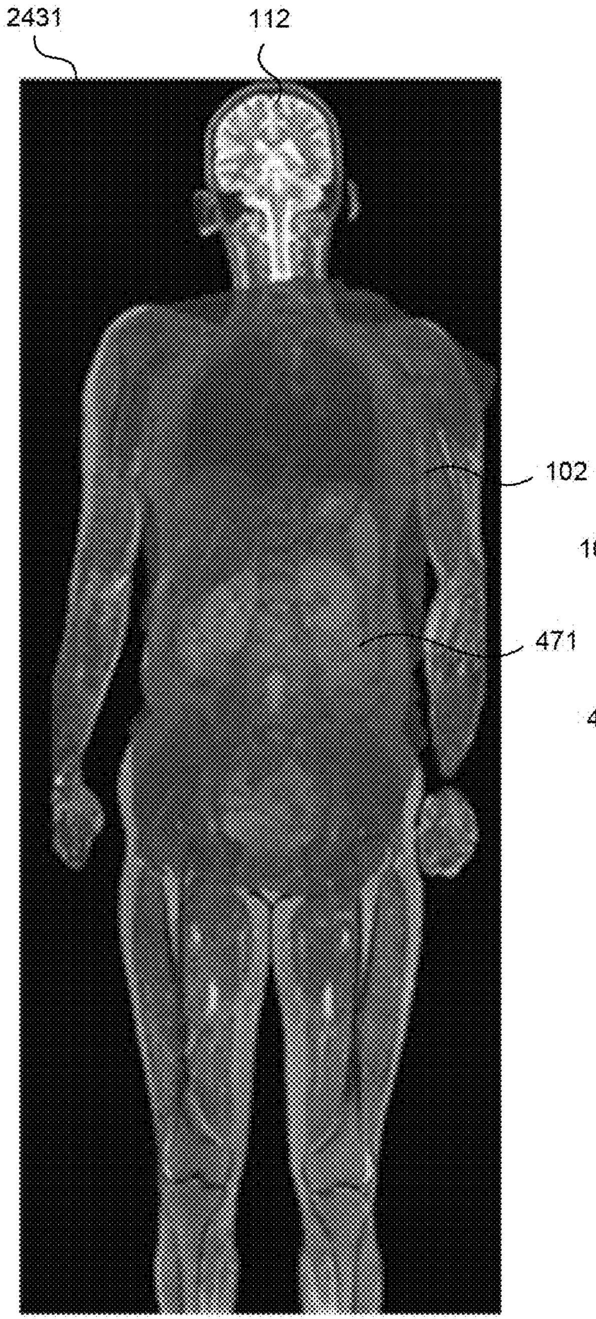
FIG. 24 is a schematic view of an MRI image of a region of interest generated from images captured using an image capture device of a video-based patient monitoring system configured in accordance with various embodiments of the present technology.
Figure 25:
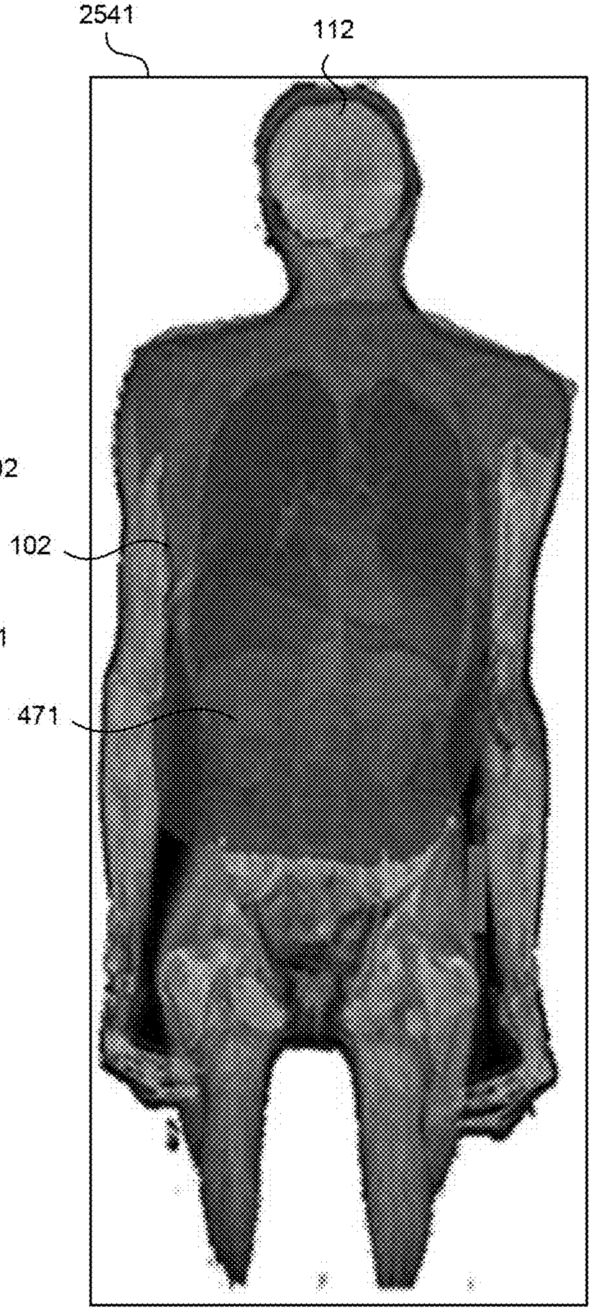
FIG. 25 is a schematic view of a CT image of a region of interest generated from images captured using an image capture device of a video-based patient monitoring system configured in accordance with various embodiments of the present technology.

As shown in FIGS. 21-25, the visualizations of the patient's breathing can be overlaid onto a variety of other image types. For example, the visualization of the ROI 102 in FIG. 21 is overlaid onto a depth image 2101 of a patient 112; the visualization of the ROI 102 in FIG. 22 is overlaid onto an RGB image 2211 of the patient 112; the visualization of the ROI 102 in FIG. 23 is overlaid onto an infrared image 2321 of the patient 112; the visualization of the ROI 102 in FIG. 24 is overlaid onto an MRI image 2431 of the patient 112; and the visualization of the ROI 102 in FIG. 25 is overlaid onto a CT image 2541 of the patient 112. In these and other embodiments, visualizations of the ROI 102 can be displayed alongside and/or can be overlaid onto these and/or other image types (e.g., ultrasound) of the patient 112 than shown in FIGS. 21-25. These other images can be used during surgical or diagnostic procedures (such as a CT scan, biopsy, surgery, etc.), and the ROI overlay enables users (e.g., clinicians, nurses, etc.) to visually monitor a patient's breathing cycles (or other respiratory parameters) alongside the surgical or other procedure. For example, the system can provide information regarding a patient's breathing while the patient is anesthetized and/or while a portion (e.g., the chest or abdomen) of the patient is under a blanket or is otherwise covered during surgery.

In some embodiments, a user can select which image type to view the patient 112 and/or the user can toggle the display of the visualization of the ROI 102 on and/or off. In these and other embodiments, the user can define the ROI 102 within a selected image type. For example, a user can define a ROI 102 to align with a patient's torso within an RGB image of the patient 112. This can be helpful, for example, when a portion of the patient 112 is hidden from an image capture device's FOV (e.g., when a patient 112 is underneath a blanket). Although the visualizations of the patient's breathing are confined to regions within the ROI 102 in the images of the patients 112 in FIGS. 21-25, the visualizations of the patient's breathing can be overlaid onto regions outside of the ROI 102 in other embodiments in addition to or in lieu of regions within the ROI 102. In these and still other embodiments, regions outside of the ROI 102 can be displayed with a different visual indicator (e.g. a different color) than the visual indicators overlaid onto regions within the ROI 102.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. Furthermore, the various embodiments described herein can also be combined to provide further embodiments. Moreover, any one of the visual indicators (e.g., colors) described herein can be the same visual indicator (e.g., color) as and/or a different visual indicator (e.g., color) than any one of the other visual indicators (e.g., colors) described herein. Any one of the audio and/or visual alerts/alarms described herein can be the same as and/or a different than any one of the other audio and/or visual alerts/alarms described herein. In addition, one or more other colors, sequences of colors, patterns, shades, densities, intensities, concentrations, and/or visual indicators than shown in the embodiments illustrated herein are within the scope of the present technology. Furthermore, any one of the visual indicators described herein can be spatially uniform across an ROI in a generated image, can spatially vary across an ROI in a generated image, can remain constant throughout all or a portion of a patient's breathing cycle, and/or can vary throughout all or a portion of the patient's breathing cycle. Any of the displayed visual indicators can be displayed apart (e.g., independent) from the one or more regions of an ROI on which they are based. As an example, the visual indicators can be displayed within a box having a different (e.g., smaller or larger) area than the ROI or a region within the ROI. The box can be displayed over the ROI, at another location (e.g., apart from), or separate from the ROI on the display. The visual indicators can be based on one or more regions of the ROI. The visual indicators can be displayed within, fill in, or empty from the box to provide a user information about a patient's breathing cycles.

The systems and methods described herein can be provided in the form of tangible and non-transitory machine-readable medium or media (such as a hard disk drive, hardware memory, etc.) having instructions recorded thereon for execution by a processor or computer. The set of instructions can include various commands that instruct the computer or processor to perform specific operations such as the methods and processes of the various embodiments described here. The set of instructions can be in the form of a software program or application. The computer storage media can include volatile and non-volatile media, and removable and non-removable media, for storage of information such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. The components can be separate from each other, or various combinations of components can be integrated together into a monitor or processor or contained within a workstation with standard computer hardware (for example, processors, circuitry, logic circuits, memory, and the like). The system can include processing devices such as microprocessors, microcontrollers, integrated circuits, control units, storage media, and other hardware.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded. Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

From the foregoing, it will also be appreciated that various modifications can be made without deviating from the technology. For example, various components of the technology can be further divided into subcomponents, or various components and functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A method for visualizing breathing activity of a patient, the method comprising:

capturing, using a depth-sensing camera, depth images in a field of view encompassing at least a portion of a patient;

defining, using a processor, a region of interest (ROI) in the field of view, the ROI corresponding to a torso of the patient;

measuring changes in depth within the ROI, the changes in depth representing movements of the patient associated with breathing;

generating, from the measured changes in depth, a breathing parameter signal of the patient;

assigning to the ROI a visual indicator that varies in real-time with the breathing parameter signal;

displaying, on a display, a second type of image of the patient that differs from the depth images; and overlaying the ROI on the second type of image, wherein assigning to the ROI the visual indicator that varies in real-time with the breathing parameter signal comprises filling the ROI with an amount of the visual indicator that corresponds to an amount of air in the patient's lungs.

2. The method of claim 1, wherein the visual indicator comprises a first visual indicator that indicates an outward movement of the patient's torso within the ROI and a second visual indicator that indicates an inward movement of the patient's torso within the ROI.

3. The method of claim 1, wherein defining the ROI comprises determining a skeleton outline of the patient.

4. The method of claim 1, wherein defining the ROI comprises recognizing one or more characteristic features of the patient.

5. The method of claim 1, wherein defining the ROI comprises extrapolating from a point on the patient.

6. The method of claim 1, wherein defining the ROI comprises identifying a face of the patient in the depth image and inferring a position of the ROI from a spatial or proportional relationship with the patient's face.

7. The method of claim 1, wherein the breathing parameter signal comprises tidal volume.

8. The method of claim 7, wherein the tidal volume is generated by integrating changes in volume computed across the ROI.

9. The method of claim 1, wherein the visual indicator exaggerates or emphasizes changes in depth in the ROI.

10. The method of claim 9, wherein the visual indicator indicates an amount of excursion of a region within the ROI.

11. The method of claim 1, wherein the visual indicator provides an indication of a current phase of breathing.

12. The method of claim 1, wherein the second type of image comprises an RGB image, an infrared image, a CT image, or an MRI image.

13. A method for visualizing breathing activity of a patient, the method comprising:

capturing, using a depth-sensing camera, depth images in a field of view encompassing at least a portion of a patient;

defining, using a processor, a region of interest (ROI) in the field of view, the ROI corresponding to a torso of the patient;

measuring changes in depth within the ROI, the changes in depth representing movements of the patient associated with breathing;

generating, from the measured changes in depth, a tidal volume signal of the patient;

assigning to the ROI a visual indicator that varies in real-time with the tidal volume signal;

overlaying the ROI with the visual indicator onto a displayed image;

setting a threshold target tidal volume representing a volume of air below which the patient is breathing abnormally; and upon determining that the generated tidal volume signal passes below the threshold target tidal volume, changing the visual indicator or triggering an alarm.

14. The method of claim 13, wherein the displayed image comprises a depth image, an RGB image, an infrared image, a CT image, or an MRI image.

15. The method of claim 13, wherein the method comprises both changing the visual indicator and triggering an alarm upon determining that the generated tidal volume signal passes below the threshold target tidal volume.

16. A method for visualizing breathing activity of a patient, the method comprising:

capturing, using a depth-sensing camera, depth information comprising depth images in a field of view encompassing a portion of a patient;

defining, using a processor, a region of interest (ROI) in the field of view, the ROI corresponding to the portion of the patient;

measuring, from the depth information, changes in depth within the ROI, the changes in depth representing movements of the patient associated with breathing;

generating, from the measured changes in depth, a breathing parameter signal of the patient;

assigning to the ROI a visual indicator that varies in real-time with the breathing parameter signal;

displaying, on a display, a second type of image of the patient that differs from the depth images; and overlaying the ROI on the second type of image, wherein assigning to the ROI the visual indicator that varies in real-time with the breathing parameter signal comprises filling the ROI with an amount of the visual indicator that corresponds to a position along a breathing cycle of the patient.

* * * * *